(12) United States Patent
Sun et al.

(10) Patent No.: US 9,249,181 B2
(45) Date of Patent: Feb. 2, 2016

(54) C-TERMINAL AMIDATION OF POLYPEPTIDES

(75) Inventors: Chengzao Sun, San Diego, CA (US);
Behrouz Bruce Forood, San Diego, CA (US); Gary Luo, San Diego, CA (US);
Soumitra S. Ghosh, San Diego, CA (US)

(73) Assignees: Amylin Pharmaceuticals, LLC, Wilmington, DE (US); AstraZeneca Pharmaceuticals LP, Wilmington, DE (US)

( * ) Notice: Subject to any disclaimer, the term of this patent is extended or adjusted under 35 U.S.C. 154(b) by 107 days.

(21) Appl. No.: 13/822,821

(22) PCT Filed: Sep. 8, 2011

(86) PCT No.: PCT/US2011/050754
§ 371 (c)(1),
(2), (4) Date: Nov. 7, 2013

(87) PCT Pub. No.: WO2012/036962
PCT Pub. Date: Mar. 22, 2012

(65) Prior Publication Data
US 2014/0058070 A1 Feb. 27, 2014

Related U.S. Application Data

(60) Provisional application No. 61/382,391, filed on Sep. 13, 2010.

(51) Int. Cl.
*C07K 1/00* (2006.01)
*C07K 1/107* (2006.01)
*C07D 311/88* (2006.01)
*C07C 211/27* (2006.01)

(52) U.S. Cl.
CPC .............. *C07K 1/003* (2013.01); *C07C 211/27* (2013.01); *C07D 311/88* (2013.01); *C07K 1/107* (2013.01)

(58) Field of Classification Search
CPC ................................ C07K 1/003; C07K 1/107
See application file for complete search history.

(56) References Cited

U.S. PATENT DOCUMENTS

| 5,580,751 A | 12/1996 | Buchardt et al. |
| 5,610,144 A | 3/1997 | Capet et al. |
| 6,307,018 B1 | 10/2001 | Kent et al. |

OTHER PUBLICATIONS

Kawakami et al. (Peptide Science, vol. 42nd, Pub date 2006; pp. 5-8).*
Botti et al. (Tetrahedron Lett. 42 (2001) 1831-1833).*

* cited by examiner

*Primary Examiner* — Valerie Rodriguez-Garcia
(74) *Attorney, Agent, or Firm* — Mintz, Levin, Cohn, Ferris Glovsky and Popeo, P.C.

(57) ABSTRACT

There are provided compounds and methods for amidating the C-terminus of a polypeptide. The methods include reacting a polypeptide which includes a C-terminal thioester or C-terminal selenoester with any one of a defined set of auxiliary molecules under conditions suitable to produce a polypeptide adduct which includes the auxiliary molecule chemically bound at the C-terminal of the polypeptide. The auxiliary molecule can be a substituted or unsubstituted 2-phenyl-2-amino ethanethiol, a substituted or unsubstituted 2-phenyl-2-amino ethaneselenol, or a substituted xanthene. In the subsequent step, a portion of the auxiliary molecule is removed from the C-terminal of the polypeptide adduct and leaving the amide nitrogen under conditions suitable to form a C-terminal free amide polypeptide.

19 Claims, No Drawings

C-TERMINAL AMIDATION OF POLYPEPTIDES

CROSS-REFERENCE TO RELATED APPLICATIONS

This application claims is a national phase of International Application No. PCT/US2011/050754, filed Sep. 8, 2011, which claims the benefit of priority under 35 USC §119 to U.S. Provisional Application No. 61/382,391, filed on Sep. 13, 2010, the disclosure of each of which is incorporated herein by reference in its entirety.

FIELD

There are provided new compounds, new compositions and new methods for performing post-translational amide formation for polypeptides.

BACKGROUND

Many active polypeptide therapeutics exist that have greater stability or are functional only in the C-terminal amide form, and not in the acid form. While short polypeptide amides can be conveniently made by solid phase synthesis there is still a great need for manufacturing processes able to produce longer peptides and polypeptides using cost-effective recombinant procedures coupled with post-translational amidation.

Chemical or enzymatic methods can be utilized for post-translational amide formation. Methods for amidation include the following: (a) chemical cleavage and amidation with palladium or cyanylation reagents, (b) enzymatic amidation with peptidylglycine α-amidating monooxygenase (PAM), and (c) C-terminal transpeptidation with carboxypeptidase Y. However, each of these methods carries significant disadvantages. The first method carries the disadvantage of requiring specific sequences to be incorporated into the C-terminus of the peptide, and additionally offers yields in the range of only 8-30%. The second method can effectively convert a C-terminal glycine extended peptide to an amide in some instances, but carries the disadvantage that the preparation of the required PAM enzyme is time consuming and expensive. Moreover, not all polypeptides are soluble at a pH at which the enzymatic reaction occurs. The C-terminal transpeptidation reaction is limited to the use of only a few amino acids as nucleophiles, and yields for this method can be very low and are dependent on the amino acid located on the C-terminus.

Thus, there is a need for a general and easy method of performing C-terminal amidation on recombinantly expressed polypeptides.

BRIEF SUMMARY OF THE INVENTION

There are provided methods for producing a C-terminus free amide polypeptide. The methods include contacting a C-terminal thioester with a substituted or unsubstituted 2-phenyl-2-amino ethanethiol, thereby forming a C-terminal substituted amide polypeptide substituted with a 2-phenyl-2-amino ethanethiol moiety, or contacting a C-terminal selenoester with a substituted or unsubstituted 2-phenyl-2-amino ethaneselenol, thereby forming a C-terminal substituted amide polypeptide substituted with a 2-phenyl-2-amino ethaneselenol moiety. In a subsequent step, the 2-phenyl-2-amino ethanethiol moiety or 2-phenyl-2-amino ethaneselenol moiety is removed, thereby forming the C-terminal free amide polypeptide.

In further aspects, there are provided methods for producing a C-terminal free amide polypeptide, which include the step of contacting a C-terminal thioester polypeptide or a C-terminal selenoester polypeptide with a compound having the structure of Formula (III) or Formula (IV), respectively, as described herein, thereby forming a C-terminal substituted amide polypeptide substituted with a substituted xanthene moiety. In a subsequent step, the substituted xanthene moiety is removed, thereby forming the C-terminal free amide polypeptide.

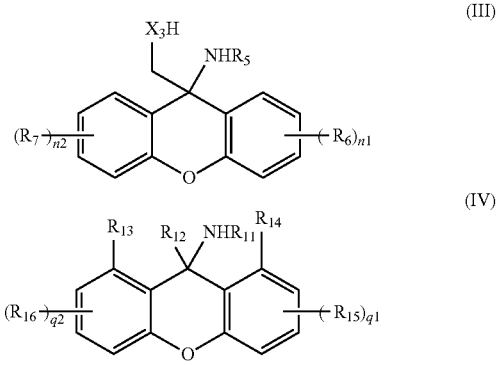

In another aspect, there are provided compounds of any of Formulae (I), (III), (IV), (V), (VI) or (VIII), as described herein.

BRIEF DESCRIPTION OF THE DRAWINGS

Not applicable.

DETAILED DESCRIPTION OF THE INVENTION

I. Definitions

The abbreviations used herein have their conventional meaning within the chemical and biological arts. The chemical structures and formulae set forth herein are constructed according to the standard rules of chemical valency known in the chemical arts.

Where substituent groups are specified by their conventional chemical formulae, written from left to right, they equally encompass the chemically identical substituents that would result from writing the structure from right to left, e.g., —CH$_2$O— is equivalent to —OCH$_2$—.

The term "alkyl," by itself or as part of another substituent, means, unless otherwise stated, a straight (i.e., unbranched) or branched chain, or combination thereof, which may be fully saturated, mono- or polyunsaturated and can include di- and multivalent radicals, having the number of carbon atoms designated (i.e., C$_1$-C$_{10}$ means one to ten carbons). Examples of saturated hydrocarbon radicals include, but are not limited to, groups such as methyl, ethyl, n-propyl, isopropyl, n-butyl, t-butyl, isobutyl, sec-butyl, (cyclohexyl)methyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. An alkoxy is an alkyl attached to the remainder of the molecule via an oxygen linker (—O—).

The term "alkylene," by itself or as part of another substituent, means, unless otherwise stated, a divalent radical derived from an alkyl, as exemplified, but not limited by, —$CH_2CH_2CH_2CH_2$—. Typically, an alkyl (or alkylene) group will have from 1 to 24 carbon atoms, with those groups having 10 or fewer carbon atoms being preferred in the present invention. A "lower alkyl" or "lower alkylene" is a shorter chain alkyl or alkylene group, generally having eight or fewer carbon atoms.

The term "alkenyl" refers to mono- or polyunsaturated alkyl having one or more double bonds. The term "alkynyl" refers to mono- or polyunsaturated alkyl having one or more triple bonds.

The term "heteroalkyl," by itself or in combination with another term, means, unless otherwise stated, a stable straight or branched chain, or combinations thereof, consisting of at least one carbon atom and at least one heteroatom selected from the group consisting of O, N, P, Si, and S, and wherein the nitrogen and sulfur atoms may optionally be oxidized, and the nitrogen heteroatom may optionally be quaternized. The heteroatom(s) O, N, P, S, and Si may be placed at any interior position of the heteroalkyl group or at the position at which the alkyl group is attached to the remainder of the molecule. Examples include, but are not limited to: —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$, —S(O)—$CH_3$, —$CH_2$—$CH_2$—S(O)$_2$—$CH_3$, —CH=CH—O—$CH_3$, —Si($CH_3$)$_3$, —$CH_2$—CH=N—$OCH_3$, —CH=CH—N($CH_3$)—$CH_3$, —O—$CH_3$, —O—$CH_2$—$CH_3$, and —CN. Up to two heteroatoms may be consecutive, such as, for example, —$CH_2$—NH—$OCH_3$.

Similarly, the term "heteroalkylene," by itself or as part of another substituent, means, unless otherwise stated, a divalent radical derived from heteroalkyl, as exemplified, but not limited by, —$CH_2$—$CH_2$—S—$CH_2$—$CH_2$— and —$CH_2$—S—$CH_2$—$CH_2$—NH—$CH_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)$_2$R— represents both —C(O)$_2$R'— and —R'C(O)$_2$—. As described above, heteroalkyl groups, as used herein, include those groups that are attached to the remainder of the molecule through a heteroatom, such as —C(O)R', —C(O)NR', —NR'R", —OR', —SR', and/or —SO$_2$R'. Where "heteroalkyl" is recited, followed by recitations of specific heteroalkyl groups, such as —NR'R" or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like.

The terms "cycloalkyl" and "heterocycloalkyl," by themselves or in combination with other terms, mean, unless otherwise stated, cyclic versions of "alkyl" and "heteroalkyl," respectively. Additionally, for heterocycloalkyl, a heteroatom can occupy the position at which the heterocycle is attached to the remainder of the molecule. Examples of cycloalkyl include, but are not limited to, cyclopropyl, cyclobutyl, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. A "cycloalkylene" and a "heterocycloalkylene," alone or as part of another substituent, means a divalent radical derived from a cycloalkyl and heterocycloalkyl, respectively.

The terms "halo" or "halogen," by themselves or as part of another substituent, mean, unless otherwise stated, a fluorine, chlorine, bromine, or iodine atom. Additionally, terms such as "haloalkyl" are meant to include monohaloalkyl and polyhaloalkyl. For example, the term "halo($C_1$-$C_4$)alkyl" includes, but is not limited to, fluoromethyl, difluoromethyl, trifluoromethyl, 2,2,2-trifluoroethyl, 4-chlorobutyl, 3-bromopropyl, and the like.

The term "acyl" means, unless otherwise stated, —C(O)R where R is a substituted or unsubstituted alkyl, substituted or unsubstituted cycloalkyl, substituted or unsubstituted heteroalkyl, substituted or unsubstituted heterocycloalkyl, substituted or unsubstituted aryl, or substituted or unsubstituted heteroaryl.

The term "aryl" means, unless otherwise stated, a polyunsaturated, aromatic, hydrocarbon substituent, which can be a single ring or multiple rings (preferably from 1 to 3 rings) that are fused together (i.e., a fused ring aryl) or linked covalently. A fused ring aryl refers to multiple rings fused together wherein at least one of the fused rings is an aryl ring. The term "heteroaryl" refers to aryl groups (or rings) that contain from one to four heteroatoms selected from N, O, and S, wherein the nitrogen and sulfur atoms are optionally oxidized, and the nitrogen atom(s) are optionally quaternized. Thus, the term "heteroaryl" includes fused ring heteroaryl groups (i.e., multiple rings fused together wherein at least one of the fused rings is a heteroaromatic ring). A 5,6-fused ring heteroarylene refers to two rings fused together, wherein one ring has 5 members and the other ring has 6 members, and wherein at least one ring is a heteroaryl ring. Likewise, a 6,6-fused ring heteroarylene refers to two rings fused together, wherein one ring has 6 members and the other ring has 6 members, and wherein at least one ring is a heteroaryl ring. And a 6,5-fused ring heteroarylene refers to two rings fused together, wherein one ring has 6 members and the other ring has 5 members, and wherein at least one ring is a heteroaryl ring. A heteroaryl group can be attached to the remainder of the molecule through a carbon or heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below. An "arylene" and a "heteroarylene," alone or as part of another substituent, mean a divalent radical derived from an aryl and heteroaryl, respectively.

For brevity, the term "aryl" when used in combination with other terms (e.g., aryloxy, arylthioxy, arylalkyl) includes both aryl and heteroaryl rings as defined above. Thus, the term "arylalkyl" is meant to include those radicals in which an aryl group is attached to an alkyl group (e.g., benzyl, phenethyl, pyridylmethyl, and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like).

The term "oxo," as used herein, means an oxygen that is double bonded to a carbon atom.

The term "alkylsulfonyl," as used herein, means a moiety having the formula —S($O_2$)—R', where R' is an alkyl group as defined above. R' may have a specified number of carbons (e.g., "$C_1$-$C_4$ alkylsulfonyl").

Each of the above terms (e.g., "alkyl," "heteroalkyl," "aryl," and "heteroaryl") includes both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to, —OR', =O, =NR', —NR'R", —SR', -halogen, —SiR'R"R"', —OC(O)R', —C(O)R', —$CO_2$R', —CONR'R", —OC(O)NR'R", —NR"C(O)R', —NR'—C(O) NR"R"', —NR"C(O)$_2$R', —NR—C(NR'R"R"')=NR"", —NR—C(NR'R")=NR"', —S(O)R', —S(O)$_2$R', —S(O)$_2$NR'R", —NRSO$_2$R', —CN, and —$NO_2$ in a number ranging from zero to (2 m'+1), where m' is the total number of carbon atoms in such radical. R', R", R"', and R"" each preferably independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted alkyl, alkoxy, or thioalkoxy groups, or arylalkyl groups. When a compound of the invention includes more than one R group, for example, each of the R groups is independently selected as are each R', R", R"', and R"" group when more than one of these groups is present. When R' and R" are attached to the same nitrogen atom, they can be combined with the nitrogen atom to form a 4-, 5-, 6-, or 7-membered ring. For example, —NR'R" includes, but is not limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —$CF_3$ and —$CH_2CF_3$) and acyl (e.g., —C(O)$CH_3$, —C(O)$CF_3$, —C(O)$CH_2OCH_3$, and the like).

Similar to the substituents described for the alkyl radical, substituents for the aryl and heteroaryl groups are varied and are selected from, for example: —OR', —NR'R", —SR', -halogen, —SiR'R"R"', —OC(O)R', —C(O)R', —$CO_2$R', —CONR'R", —OC(O)NR'R", —NR"C(O)R', —NR'—C(O)NR"R"', —NR"C(O)$_2$R', —NR—C(NR'R"R"')=NR"", —NR—C(NR'R")=NR"', —S(O)R', —S(O)$_2$R', —S(O)$_2$NR'R", —NRSO$_2$R', —CN, —$NO_2$, —R', —$N_3$, —CH(Ph)$_2$, fluoro($C_1$-$C_4$)alkoxy, and fluoro($C_1$-$C_4$)alkyl, in a number ranging from zero to the total number of open valences on the aromatic ring system; and where R', R", R"', and R"" are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. When a compound of the invention includes more than one R group, for example, each of the R groups is independently selected as are each R', R", R"', and R"" groups when more than one of these groups is present.

Two or more substituents may optionally be joined to form aryl, heteroaryl, cycloalkyl, or heterocycloalkyl groups. Such so-called ring-forming substituents are typically, though not necessarily, found attached to a cyclic base structure. In one embodiment, the ring-forming substituents are attached to adjacent members of the base structure. For example, two ring-forming substituents attached to adjacent members of a cyclic base structure create a fused ring structure. In another embodiment, the ring-forming substituents are attached to a single member of the base structure. For example, two ring-forming substituents attached to a single member of a cyclic base structure create a spirocyclic structure. In yet another embodiment, the ring-forming substituents are attached to non-adjacent members of the base structure.

Two of the substituents on adjacent atoms of the aryl or heteroaryl ring may optionally form a ring of the formula -T-C(O)—(CRR')$_q$—U—, wherein T and U are independently —NR—, —O—, —CRR'—, or a single bond, and q is an integer of from 0 to 3. Alternatively, two of the substituents on adjacent atoms of the aryl or heteroaryl ring may optionally be replaced with a substituent of the formula -A-($CH_2$)$_r$—B—, wherein A and B are independently —CRR'—, —O—, —NR—, —S—, —S(O)—, —S(O)$_2$—, —S(O)$_2$NR'—, or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X'—(C"R"')$_d$—, where s and d are independently integers of from 0 to 3, and X' is —O—, —NR'—, —S—, —S(O)—, —S(O)$_2$—, or —S(O)$_2$NR'—. The substituents R, R', R", and R"' are preferably independently selected from hydrogen, substituted or unsubstituted alkyl, substituted or unsubstituted cycloalkyl, substituted or unsubstituted heterocycloalkyl, substituted or unsubstituted aryl, and substituted or unsubstituted heteroaryl.

As used herein, the terms "heteroatom" or "ring heteroatom" are meant to include oxygen (O), nitrogen (N), sulfur (S), phosphorus (P), and silicon (Si).

A "substituent group," as used herein, means a group selected from the following moieties:

(A) —OH, —$NH_2$, —SH, —CN, —$CF_3$, —$NO_2$, oxo, halogen, unsubstituted alkyl, unsubstituted heteroalkyl, unsubstituted cycloalkyl, unsubstituted heterocycloalkyl, unsubstituted aryl, unsubstituted heteroaryl, and (B) alkyl, heteroalkyl, cycloalkyl, heterocycloalkyl, aryl, and heteroaryl, substituted with at least one substituent selected from:

(i) oxo, —OH, —$NH_2$, —SH, —CN, —$CF_3$, —$NO_2$, halogen, unsubstituted alkyl, unsubstituted heteroalkyl, unsubstituted cycloalkyl, unsubstituted heterocycloalkyl, unsubstituted aryl, unsubstituted heteroaryl, and (ii) alkyl, heteroalkyl, cycloalkyl, heterocycloalkyl, aryl, and heteroaryl, substituted with at least one substituent selected from:

(a) oxo, —OH, —$NH_2$, —SH, —CN, —$CF_3$, —$NO_2$, halogen, unsubstituted alkyl, unsubstituted heteroalkyl, unsubstituted cycloalkyl, unsubstituted heterocycloalkyl, unsubstituted aryl, unsubstituted heteroaryl, and (b) alkyl, heteroalkyl, cycloalkyl, heterocycloalkyl, aryl, or heteroaryl, substituted with at least one substituent selected from: oxo, —OH, —$NH_2$, —SH, —CN, —$CF_3$, —$NO_2$, halogen, unsubstituted alkyl, unsubstituted heteroalkyl, unsubstituted cycloalkyl, unsubstituted heterocycloalkyl, unsubstituted aryl, and unsubstituted heteroaryl.

A "size-limited substituent" or "size-limited substituent group," as used herein, means a group selected from all of the substituents described above for a "substituent group," wherein each substituted or unsubstituted alkyl is a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_4$-$C_8$ cycloalkyl, and each substituted or unsubstituted heterocycloalkyl is a substituted or unsubstituted 4 to 8 membered heterocycloalkyl.

A "lower substituent" or "lower substituent group," as used herein, means a group selected from all of the substituents described above for a "substituent group," wherein each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_5$-$C_7$ cycloalkyl, and each substituted or unsubstituted heterocycloalkyl is a substituted or unsubstituted 5 to 7 membered heterocycloalkyl.

The term "pharmaceutically acceptable salts" is meant to include salts of the active compounds that are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, oxalic, methanesulfonic, and the like. Also included are salts of amino acids such as arginate and the like, and salts of organic acids like glucuronic or galactunoric acids and the like (see, for example, Berge et al., "Pharmaceutical Salts", *Journal of Pharmaceutical Science*, 1977, 66, 1-19). Certain specific compounds of the present invention contain both basic and acidic functionalities that allow the compounds to be converted into either base or acid addition salts.

Thus, the compounds of the present invention may exist as salts, such as with pharmaceutically acceptable acids. The present invention includes such salts. Examples of such salts include hydrochlorides, hydrobromides, sulfates, methanesulfonates, nitrates, maleates, acetates, citrates, fumarates, tartrates (e.g., (+)-tartrates, (−)-tartrates, or mixtures thereof including racemic mixtures), succinates, benzoates, and salts with amino acids such as glutamic acid. These salts may be prepared by methods known to those skilled in the art.

The neutral forms of the compounds are preferably regenerated by contacting the salt with a base or acid and isolating the parent compound in the conventional manner. The parent form of the compound differs from the various salt forms in certain physical properties, such as solubility in polar solvents.

In addition to salt forms, the present invention provides compounds in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Certain compounds of the present invention can exist in unsolvated forms as well as solvated forms, including hydrated forms. In general, the solvated forms are equivalent to unsolvated forms and are encompassed within the scope of the present invention. Certain compounds of the present invention may exist in multiple crystalline or amorphous forms. In general, all physical forms are equivalent for the uses contemplated by the present invention and are intended to be within the scope of the present invention.

Certain compounds of the present invention possess asymmetric carbon atoms (optical centers) or double bonds; the racemates, diastereomers, tautomers, geometric isomers, and individual isomers are encompassed within the scope of the present invention. The compounds of the present invention do not include those that are known in the art to be too unstable to synthesize and/or isolate.

The compounds of the present invention may also contain unnatural proportions of atomic isotopes at one or more of the atoms that constitute such compounds. For example, the compounds may be radiolabeled with radioactive isotopes, such as for example tritium ($^3H$), iodine-125 ($^{125}I$), or carbon-14 ($^{14}C$). All isotopic variations of the compounds of the present invention, whether radioactive or not, are encompassed within the scope of the present invention.

The symbol "⌇" denotes the point of attachment of a chemical moiety to the remainder of a molecule or chemical formula.

The terms "protein", "peptide", "protein/peptide", and "polypeptide" are used interchangeably throughout the disclosure and each has the same meaning for purposes of this disclosure. Each term refers to an organic compound made of a linear chain of two or more amino acids. The compound may have ten or more amino acids; twenty-five or more amino acids; fifty or more amino acids; one hundred or more amino acids, and even two hundred or more amino acids. The skilled artisan will appreciate that polypeptides generally comprise fewer amino acids than proteins, although there is no art-recognized cut-off point of the number of amino acids that distinguish a polypeptides and a protein; that polypeptides may be made by chemical synthesis or recombinant methods; and that proteins are generally made in vitro by recombinant methods as known in the art.

The terms "amidated polypeptide," "C-terminal free amide polypeptide" and the like as used herein refer to polypeptides that have an amino group (—$NH_2$) on the C-terminal amino acid residue of the polypeptide.

The polypeptides that can be used in the methods described herein may be any known in the art, such as amylin and analogs thereof including e.g., pramlintide, davalintide and analogs thereof, exendin-4 and analogs thereof, glucagon-like peptide-1 (GLP-1(7-37)) and analogs thereof; meterleptin and analogs thereof; pramlintide and analogs thereof; peptide-YY (PYY(3-36)) and analogs thereof; gastric inhibitory polypeptide (GIP) and analogs thereof; insulin and analogs thereof; human growth hormone (HGH) and analogs thereof; erythropoietin (EPO) and analogs thereof; cholescystokinin (CCK) and analogs thereof; glucagon-like peptide-2 (GLP-2) and analogs thereof; GLP-1/glucagon chimeric peptides; GLP-1/GIP chimeric peptides; neurotensin and analogs thereof; urocortins and analogs thereof; neuromedins and analogs thereof; hybrid proteins, and the like. The term "hybrid" in the context of a polypeptide refers the combination of two or more polypeptides, as described herein. The combination can be either through covalent or non-covalent attachment and, optionally, through appropriate spacers and/or linkers. Exemplary methods for combining polypeptides are described in PCT Published Appl. No. WO 2007/022123, filed Aug. 11, 2006, and WO 2005/077072, filed Feb. 11, 2005, each of which is incorporated herein by reference in its entirety and for all purposes.

Amylins.

Amylin is a peptide hormone synthesized by pancreatic β-cells that is cosecreted with insulin in response to nutrient intake. See e.g., U.S. Pat. No. 5,124,314, U.S. Pat. No. 5,175,145, U.S. Pat. No. 5,367,052. The sequence of amylin is highly preserved across mammalian species, with structural similarities to calcitonin gene-related peptide (CGRP), the calcitonins, the intermedins, and adrenomedullin, as known in the art. The glucoregulatory actions of amylin complement those of insulin by regulating the rate of glucose appearance in the circulation via suppression of nutrient-stimulated glucagon secretion and slowing gastric emptying. In insulin-treated patients with diabetes, pramlintide, a synthetic and equipotent analogue of human amylin, reduces postprandial glucose excursions by suppressing inappropriately elevated postprandial glucagon secretion and slowing gastric emptying. The sequences of rat amylin, human amylin and pramlintide follow:

```
                                            (SEQ ID NO: 1)
KCNTATCATQRLANFLVRSSNNLGPVLPPTNVGSNTY;

(SEQ ID NO: 2)
KCNTATCATQRLANFLVHSSNNFGAILSSTNVGSNTY;

(SEQ ID NO: 3)
KCNTATCATQRLANFLVHSSNNFGPILPPTNVGSNTY.
```

Davalintide.

Davalintide (also known as "AC-2307") is a potent amylin agonist useful in the treatment of a variety of disease indications. See WO 2006/083254 and WO 2007/114838, each of which is incorporated by reference herein in its entirety and for all purposes. Davalintide is a chimeric peptide, having an N-terminal loop region of amylin or calcitonin and analogs thereof, an alpha-helical region of at least a portion of an alpha-helical region of calcitonin or analogs thereof or an alpha-helical region having a portion of an amylin alpha-helical region and a calcitonin alpha-helical region or analog thereof, and a C-terminal tail region of amylin or calcitonin. The sequences of human calcitonin, salmon calcitonin and davalintide follow, respectively:

```
                                            (SEQ ID NO: 4)
CGNLSTCMLGTYTQDFNKFHTFPQTAIGVGAP;

(SEQ ID NO: 5)
CSNLSTCVLGKLSQELHKLQTYPRTNTGSGTP;

(SEQ ID NO: 6)
KCNTATCVLGRLSQELHRLQTYPRTNTGSNTY.
```

Exendins.

Exendin, exendin analogs and derivatives thereof suitable for use in the methods described herein include the compounds described in WO 2007/022123 (PCT/US2006/031724, filed Aug. 11, 2006), incorporated herein by reference and for all purposes. The exendins are peptides that are found in the salivary secretions of the Gila monster and the Mexican Bearded Lizard, reptiles that are endogenous to Arizona and Northern Mexico. Exendin-3 is present in the salivary secretions of *Heloderma horridum* (Mexican Beaded Lizard), and exendin-4 is present in the salivary secretions of *Heloderm suspectum* (Gila monster). See Eng et al, 1990, *J. Biol. Chem.*, 265:20259-62; Eng et al, 1992, *J. Biol. Chem.*, 267:7402-7405. The sequences of exendin-3 and exendin-4, respectively, follow:

```
                                            (SEQ ID NO: 7)
HSDGTFTSDLSKQMEEEAVRLFIEWLKNGGPSSGAPPPS-NH₂;

(SEQ ID NO: 8)
HGEGTFTSDLSKQMEEEAVRLFIEWLKNGGPSSGAPPPS-NH₂.
```

GLP-1.

The exendins have some sequence similarity to several members of the glucagon-like peptide family, with the highest homology, 53%, being to GLP-1[7-36]NH₂ (Goke et al, 1993, *J. Biol. Chem.*, 268:19650-55), having sequence HAEGTFTSDVSSYLEGQAAKEFIAWLVKGRG (SEQ ID NO:9), also sometimes referred to as "GLP-1", which has an insulinotropic effect, stimulating insulin secretion from pancreatic beta-cells. GLP-1 has also been reported to inhibit glucagon secretion from pancreatic alpha-cells. See e.g., Orskov et al, 1993, *Diabetes*, 42:658-61; D'Alessio et al, 1996, *J. Clin. Invest.*, 97:133-38. GLP-1 has been reported to inhibit gastric emptying (Willms B, et al., 1996, *J. Clin. Endocrinol. Metab.*, 81:327-32; Wettergren, A, et al., 1993, *Dig. Dis. Sci.* 38:665-73) and gastric acid secretion (Schjoldager, B T, et al, 1989, *Dig. Dis. Sci.*, 34:703-8; O'Halloran, D J, et al., 1990, *J. Endocrinol.*, 126:169-73; Wettergren A, et al., 1993, *Dig. Dis. Sci.*, 38:665-73). GLP-1[7-37], which has an additional glycine residue at its carboxy terminus, is reported to stimulate insulin secretion in humans. See Orskov, et al., 1993, *Diabetes*, 42:658-61. Other reports relate to the inhibition of glucagon secretion (Creutzfeldt, W O C, et al., 1996, *Diabetes Care*, 19:580-6), and a purported role in appetite control (Turton, M D, et al., 1996, *Nature*, 379(6560):69-72). A transmembrane G-protein adenylate-cyclase-coupled receptor, said to be responsible at least in part for the insulinotropic effect of GLP-1, has reportedly been cloned from a beta-cell line (Thorens, 1992, *Proc. Natl. Acad. Sci. USA* 89:8641-45). GLP-1 has been the focus of significant investigation in recent years due to its reported action on the amplification of stimulated insulin production (Byrne M M, Goke B. "Lessons from human studies with glucagon-like peptide-1: Potential of the gut hormone for clinical use". In: Fehmann H C, Goke B., 1997, *Insulinotropic Gut Hormone Glucagon-Like Peptide* 1. Basel, Switzerland: Karger, 1997: 219-33).

Meterleptin.

Leptins, leptin fragments and leptin analogs contemplated for the methods described herein include, but are not limited to, the compounds described in U.S. Pat. Nos. 5,594,101, 5,851,995, 5,691,309, 5,580,954, 5,554,727, 5,552,523, 5,559,208, 5,756,461, 6,309,853, and PCT Published Application Nos. WO 96/23517, WO 96/005309, WO 2004/039832, WO 98/55139, WO 98/12224, and WO 97/02004, each of which is incorporated herein in its entirety and for all purposes. Representative leptins contemplated for use in the methods described herein include meterleptin having the sequence:

```
                                            (SEQ ID NO: 10)
MVPIQKVQDDTKTLIKTIVTRINDISHTQSVSSKQKVTGLDFIPGLHPIL

TLSKMDQTLAVYQQILTSMPSRNVIQISNDLENLRDLLHVLAFSKSCHLP

WASGLETLDSLGGVLEASGYSTEVVALSRLQGSLQDMLWQLDLSPGC.
```

PYYs.

Pancreatic polypeptide ("PP") was discovered as a contaminant of insulin extracts and was named by its organ of origin rather than functional importance. See Kimmel et al, *Endocrinology* 83: 1323-30 (1968. PP is a 36-amino acid peptide containing distinctive structural motifs. A related peptide was subsequently discovered in extracts of intestine and named Peptide YY ("PYY") because of the N- and C-terminal tyrosines. See Tatemoto, *Proc. Natl. Acad. Sci. USA* 79: 2514-8 (1982). A third related peptide was later found in extracts of brain and named Neuropeptide Y ("NPY"). See Tatemoto, 1982, *Proc. Natl. Acad. Sci. USA* 79: 5485-9; Tatemoto et al., 1982, *Nature* 296: 659-60. The sequences of human PP, PYY and NPY, respectively, follow:

```
                                            (SEQ ID NO: 11)
APLEPVYPGDNATPEQMAQYAADLRRYINMLTRPRY-NH2

(SEQ ID NO: 12)
YPIKPEAPGEDASPEELNRYYASLRHYLNLVTRQRY-NH2

(SEQ ID NO: 13)
YPSKPDNPGEDAPAEDMARYYSALRHYINLITRQRY-NH2.
```

Gastric Inhibitory Polypeptide (GIP).

GIP, also known as glucose-dependent insulinotropic peptide, is a 42 amino acid hormone secreted by endocrine K cells of the duodenum in response to meal ingestion. Mature GIP is derived by proteolytic processing of the 153-residue prepro-GIP precursor, which maps to human locus 17q21.3-q22. Without wishing to be bound by any theory, it is believed that the principal action of GIP is the stimulation of glucose-dependent insulin secretion. The sequence of mature human GIP follows:

```
                                            (SEQ ID NO: 14)
YAEGTFISDYSIAMDKIHQQDFVNWLLAQKGKKNDWKHNITQ.
```

Insulin.

Human insulin as translated has the 110-residue sequence following: MALWMRLLPLLALLALWGPDPAAAFVN-QHLCGSHLVEALYLVCGERGFFYTPKTRRE AEDLQVGQVELGGGPGAGSLQPLA-LEGSLQKRGIVEQCCTSICSLYQLENYCN (SEQ ID NO:15). See NCBI locus AAA59182.1. As well known in the art, insulin undergoes post-translational processing prior to formation of the biological active species. The terms "biologically active compound" and the like refer in the customary sense to compounds, e.g., polypeptides and the like, which can elicit a biological response.

Human Growth Hormone (HGH).

Human growth hormone (HGH) is translated as a 217-residue sequence as follows:

```
                                            (SEQ ID NO: 16)
MATGSRTSLLLAFGLLCLPWLQEGSAFPTIPLSRLFDNAMLRAHRLHQLA

FDTYQEFEEAYIPKEQKYSFLQNPQTSLCFSESIPTPSNREETQQKSNLE

LLRISLLLIQSWLEPVQFLRSVFANSLVYGASDSNVYDLLKDLEEGIQTL

MGRLEDGSPRTGQIFKQTYSKFDTNSHNDDALLKNYGLLYCFRKDMDKVE

TFLRIVQCRSVEGSCGF.
```

See NCBI locus AAA986178.1.

Erthyropoietin (EPO).

A synthetic construct of human erthyropoietin (EPO) has the sequence

```
                                            (SEQ ID NO: 17)
MATGSRTSLLLAFGLLCLPWLQEGSAFPTIPLSRLFDNAMLRAHRLHQLA

FDTYQEFEEAYIPKEQKYSFLQNPQTSLCFSESIPTPSNREETQQKSNLE

LLRISLLLIQSWLEPVQFLRSVFANSLVYGASDSNVYDLLKDLEEGIQTL

MGRLEDGSPRTGQIFKQTYSKFDTNSHNDDALLKNYGLLYCFRKDMDKVE

TFLRIVQCRSVEGSCGF.
```

See NCIB locus ACJ06770.1.

Cholecystokinin (CCK).

Human cholecystokinin (CCK) is translated as a 115-residue sequence CCK(1-115): MNSGVCLCVLMAVLAA-GALTQPVPPADPAGSGLQRAEEAPRRQL-RVSQRTDGESRAHL GALLARYIQQARKAPSGRMSIVKN-LQNLDPSHRISDRDYMGWMDFGRRSAEEYEYPS (SEQ ID NO:18), which includes a 20-residue N-terminal signal. Mature forms of human CCK include CCK(46-103) ["CCK(58)"], CCK(65-103) ["CCK(39)"], CCK71-103) ["CCK(33)"], CCK(92-103) ["CCK(12)"], and CCK(96-103) ["CCK(8)"]. See NCIB locus CAG47022.1.

Glucagon-Like Peptide-2 (GLP-2).

Mature human GLP-2 has the sequence HADGSFS-DEMNTILDNLAARDFINWLIQTKITDR (SEQ ID NO:19). See NCIB locus CAA24759.1.

Neurotensin.

Human neurotensin has the sequence

```
                                            (SEQ ID NO: 20)
MMAGMKIQLVCMLLLAFSSWSLCSDSEEEMKALEADFLTNMHTSKISKAH

VPSWKMTLLNVCSLVNNLNSPAEETGEVHEEELVARRKLPTALDGFSLEA

MLTIYQLHKICHSRAFQHWELIQEDILDTGNDKNGKEEVIKRKIPYILKR

QLYENKPRRPYILKRDSYYY.
```

See NCBI locus AAH10918.1.

Urocortin.

Human urocortin has the sequence

```
                                            (SEQ ID NO: 21)
MRQAGRAALLAALLLLVQLCPGSSQRSPEAAGVQDPSLRWSPGARNQGGG

ARALLLLLAERFPRRAGPGRLGLGTAGERPRRDNPSLSIDLTFHLLRTLL

ELARTQSQRERAEQNRIIFDSVGK.
```

See NCIB locus AAC24204.1.

Neuromedins.

Neuromedin U is translated with the sequence MLRTE-SCRPRSPAGQVAAASPLLLLLLLLAWCA-GACRGAPILPQGLQPEQQLQLWNEID DTCSSFLSID- SQPQASNALEELCFMIMGMLPKPQEQDEKDNTKRFL
FHYSKTQKLGKSN VVSSVVHPLLQLVPHLHER-
RMKRFRVDEEFQSPFASQSRGYFLFRPRNGRRSAGFI
(SEQ ID NO:22). See NCIB locus CAA53619.1 Neuromedin
S precursor has the sequence MKHLRPQFPLILAIYCFCM-
LQIPSSGFPQPLADPSDG-
LDIVQLEQLAYCLSQWAPLSRQPK DNQDIYKRFLF-
HYSRTQEATHPVKTGFPPVHPLMHLAAKLANRRMK-
RILQRGSGTAAV DFTKKDHTATWGRPFFLFRPRN-
GRNIEDEAQIQW (SEQ ID NO:23). See NCIB locus
BAD89024.1. Neuromedin B has the sequence MARRAG-
GARMFGSLLLFALLAAGVA-
PLSWDLPEPRSRASKIRVHSRGNLWATGHFMG KKS-
LEPSSPSHWGQLPTPPLRDQRLQLSHDLLGILLLKKA-
LGVSLSRPAPQIQYRRLLVQI LQK (SEQ ID NO:24). See
NCBI locus AAA59934.1.

II. Compounds

In one aspect, there is provided a compound with structure of Formula (I):

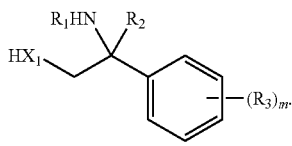

(I)

In Formula (I), $X_1$ is S or Se. $R_1$ is H, substituted or unsubstituted $C_{1-18}$ alkyl, substituted or unsubstituted $C_{5-14}$ aryl, or substituted or unsubstituted $C_{5-14}$ heteroaryl. $R_2$ is H, cyano, halo, substituted or unsubstituted $C_{1-18}$ alkyl, substituted or unsubstituted $C_{1-18}$ alkoxy, substituted or unsubstituted $C_{5-14}$ aryl, or substituted or unsubstituted $C_{5-14}$ heteroaryl. $R_3$ at each occurrence is independently H, substituted or unsubstituted $C_{1-18}$ alkyl, substituted or unsubstituted $C_{5-14}$ aryl, substituted or unsubstituted $C_{5-14}$ heteroaryl, substituted or unsubstituted $C_{1-18}$ alkoxy, cyano, nitro or halo. m is 0 to 5.

In some embodiments, $R_1$ is H, unsubstituted $C_{1-18}$ alkyl, unsubstituted $C_{5-14}$ aryl, or unsubstituted $C_{5-14}$ heteroaryl. $R_2$ is H, cyano, halo, unsubstituted $C_{1-18}$ alkyl, unsubstituted $C_{1-18}$ alkoxy, unsubstituted $C_{5-14}$ aryl, or unsubstituted $C_{5-14}$ heteroaryl. $R_3$ at each occurrence is independently H, unsubstituted $C_{1-18}$ alkyl, unsubstituted $C_{5-14}$ aryl, unsubstituted $C_{5-14}$ heteroaryl, unsubstituted $C_{1-18}$ alkoxy, cyano, nitro or halo.

In some embodiments, $R_1$ is $R_{22}$-substituted $C_{1-18}$ alkyl, $R_{22}$-substituted $C_{5-14}$ aryl, or $R_{22}$-substituted $C_{5-14}$ heteroaryl. $R_{22}$ is $R_{23}$-substituted or unsubstituted alkyl, $R_{23}$-substituted or unsubstituted heteroalkyl, $R_{23}$-substituted or unsubstituted cycloalkyl, $R_{23}$-substituted or unsubstituted heterocycloalkyl, $R_{23}$-substituted or unsubstituted aryl, or $R_{23}$-substituted or unsubstituted heteroaryl. $R_{23}$ is $R_{24}$-substituted or unsubstituted alkyl, $R_{24}$-substituted or unsubstituted heteroalkyl, $R_{24}$-substituted or unsubstituted cycloalkyl, $R_{24}$-substituted or unsubstituted heterocycloalkyl, $R_{24}$-substituted or unsubstituted aryl, or $R_{24}$-substituted or unsubstituted heteroaryl. $R_{24}$ is unsubstituted alkyl, unsubstituted heteroalkyl, unsubstituted cycloalkyl, unsubstituted heterocycloalkyl, unsubstituted aryl, or unsubstituted heteroaryl.

In some embodiments, $R_2$ is H, cyano, halo, $R_{25}$-substituted $C_{1-18}$ alkyl, $R_{25}$-substituted $C_{1-18}$ alkoxy, $R_{25}$-substituted $C_{5-14}$ aryl, or $R_{25}$-substituted $C_{5-14}$ heteroaryl. $R_{25}$ is $R_{26}$-substituted or unsubstituted alkyl, $R_{26}$-substituted or unsubstituted heteroalkyl, $R_{26}$-substituted or unsubstituted cycloalkyl, $R_{26}$-substituted or unsubstituted heterocycloalkyl, $R_{26}$-substituted or unsubstituted aryl, or $R_{26}$-substituted or unsubstituted heteroaryl. $R_{26}$ is $R_{27}$-substituted or unsubstituted alkyl, $R_{27}$-substituted or unsubstituted heteroalkyl, $R_{27}$-substituted or unsubstituted cycloalkyl, $R_{27}$-substituted or unsubstituted heterocycloalkyl, $R_{27}$-substituted or unsubstituted aryl, or $R_{27}$-substituted or unsubstituted heteroaryl. $R_{27}$ is unsubstituted alkyl, unsubstituted heteroalkyl, unsubstituted cycloalkyl, unsubstituted heterocycloalkyl, unsubstituted aryl, or unsubstituted heteroaryl.

In some embodiments, $R_3$ at each occurrence is independently H, $R_{28}$-substituted $C_{1-18}$ alkyl, $R_{28}$-substituted $C_{5-14}$ aryl, $R_{28}$-substituted $C_{5-14}$ heteroaryl, $R_{28}$-substituted $C_{1-18}$ alkoxy, cyano, nitro or halo. $R_{28}$ is $R_{29}$-substituted or unsubstituted alkyl, $R_{29}$-substituted or unsubstituted heteroalkyl, $R_{29}$-substituted or unsubstituted cycloalkyl, $R_{29}$-substituted or unsubstituted heterocycloalkyl, $R_{29}$-substituted or unsubstituted aryl, or $R_{29}$-substituted or unsubstituted heteroaryl. $R_{29}$ is $R_{30}$-substituted or unsubstituted alkyl, $R_{30}$-substituted or unsubstituted heteroalkyl, $R_{30}$-substituted or unsubstituted cycloalkyl, $R_{30}$-substituted or unsubstituted heterocycloalkyl, $R_{30}$-substituted or unsubstituted aryl, or $R_{30}$-substituted or unsubstituted heteroaryl. $R_{30}$ is unsubstituted alkyl, unsubstituted heteroalkyl, unsubstituted cycloalkyl, unsubstituted heterocycloalkyl, unsubstituted aryl, or unsubstituted heteroaryl.

In some embodiments, $R_3$ at each occurrence is independently H, substituted or unsubstituted $C_{1-18}$ alkyl, substituted or unsubstituted $C_{5-14}$ aryl, substituted or unsubstituted $C_{5-14}$ heteroaryl, substituted or unsubstituted $C_{1-18}$ alkoxy, cyano, nitro or halo.

In some embodiments, $R_1$ and $R_2$ are H, $R_3$ is methoxy or nitro, and m is 1, 2 or 3.

Further to any method or compound described herein, in some embodiments, the compound of Formula (I) is present or provided as the dimerized form with structure of Formula (II) following, wherein $X_1$, $R_1$, $R_2$, and $R_3$ at each occurrence are as defined for Formula (I), and $m_1$ and $m_2$ are independently 0 to 5. In some embodiments, the dimerized structure Formula (II) can be converted to the monomer structure Formula (I) and thus be useful in methods described herein. It is understood that a dimer to monomer conversion, as described herein, may include abstraction of one or more protons.

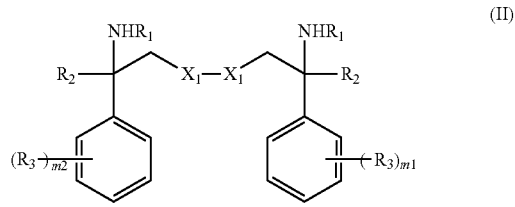

(II)

In some embodiments, $R_1$ and $R_2$ are each occurrence are H, $R_3$ at each occurrence is independently methoxy or nitro, and m1 and m2 are independently 2 or 3.

In other embodiments regarding either Formula (I) or (II), $R_1$ is H, substituted or unsubstituted $C_{1-8}$ alkyl, substituted or unsubstituted $C_{1-8}$ heteroalkyl, substituted or unsubstituted $C_{6-10}$ aryl, or substituted or unsubstituted $C_{6-10}$ heteroaryl; $R_2$ is H, cyano, halo, substituted or unsubstituted $C_1$-$C_8$ alkyl, substituted or unsubstituted $C_1$-$C_8$ heteroalkyl, substituted or unsubstituted $C_{1-8}$ alkoxy, substituted or unsubstituted $C_{6-10}$ aryl, or substituted or unsubstituted $C_{6-10}$ heteroaryl; and $R_3$ at each occurrence is H, cyano, nitro, halo, substituted or unsubstituted $C_{1-8}$ alkyl, substituted or unsubstituted $C_{1-8}$ heteroalkyl, substituted or unsubstituted $C_{1-8}$ alkoxy, substituted or unsubstituted $C_{6-10}$ aryl, or substituted or unsubstituted $C_{6-10}$ heteroaryl. m, m1 and m3 are independently 0 to 5.

In still further embodiments of the structures of either Formula (I) or (II), $R_1$ is H, substituted or unsubstituted $C_{1-4}$ alkyl, substituted or unsubstituted $C_{1-4}$ heteroalkyl, or substituted or unsubstituted $C_6$ aryl. $R_2$ is H, cyano, halo, substituted or unsubstituted $C_{1-4}$ alkyl, substituted or unsubstituted $C_{1-4}$ heteroalkyl, or unsubstituted $C_{1-4}$ alkoxy, substituted or unsubstituted $C_6$ aryl, or substituted or unsubstituted $C_6$ heteroaryl. $R_3$ is independently H, cyano, nitro, halo, substituted or unsubstituted $C_{1-4}$ alkyl, substituted or unsubstituted $C_{1-4}$ heteroalkyl, substituted or unsubstituted $C_{1-4}$ alkoxy, substituted or unsubstituted $C_6$ aryl, substituted or unsubstituted $C_6$ heteroaryl, or substituted or unsubstituted $C_{8-14}$ heteroaryl. In some embodiments, $R_3$ is methoxy.

In other embodiments of the structures of either Formula (I) or (II), $R_1$, $R_2$, and $R_3$ are independently selected from any of the above groups or sub-groups, i.e., the group of $R_1$ can be selected from any one or more of the members of any of the groupings for $R_1$ disclosed above, and likewise for $R_2$ and $R_3$. Thus, all possible combinations of $R_1$, $R_2$ and $R_3$ disclosed can be used in Formulas (I) and (II). Moreover, one or more members can be removed from any of the above disclosed groups or sub-groups of $R_1$, $R_2$, and $R_3$.

In another embodiment, the compound has a structure of Cmpd 4 or Cmpd 5 following.

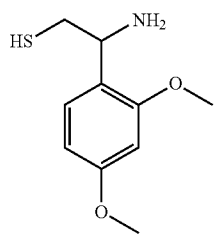

4

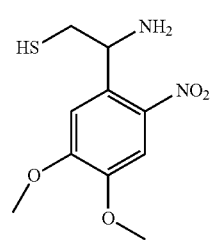

5

In another aspect, there is provided a compound with structure of Formula (V) or (VI), wherein each $R_4$ is independently H, substituted or unsubstituted $C_{1-18}$ alkyl, or substituted or unsubstituted $C_{1-18}$ heteroalkyl, and $X_2$ at each occurrence is S or Se. In some embodiments, $X_2$ is S. In some embodiments, $X_2$ is Se.

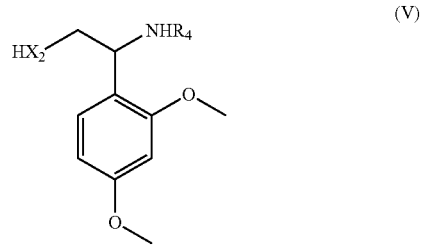

(V)

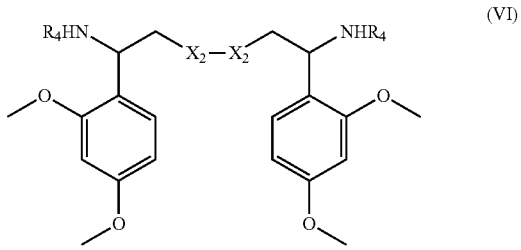

(VI)

In some embodiments, $R_4$ is independently H, unsubstituted $C_{1-18}$ alkyl, or $C_{1-18}$ heteroalkyl. In some embodiments $R_4$ at each occurrence is independently H, $R_{31}$-substituted $C_{1-18}$ alkyl, or $R_{31}$-substituted $C_{1-18}$ heteroalkyl. $R_{31}$ is $R_{32}$-substituted or unsubstituted alkyl, $R_{32}$-substituted or unsubstituted heteroalkyl, $R_{32}$-substituted or unsubstituted cycloalkyl, $R_{32}$-substituted or unsubstituted heterocycloalkyl, $R_{32}$-substituted or unsubstituted aryl, or $R_{32}$-substituted or unsubstituted heteroaryl. $R_{32}$ is $R_{33}$-substituted or unsubstituted alkyl, $R_{33}$-substituted or unsubstituted heteroalkyl, $R_{33}$-substituted or unsubstituted cycloalkyl, $R_{33}$-substituted or unsubstituted heterocycloalkyl, $R_{33}$-substituted or unsubstituted aryl, or $R_{33}$-substituted or unsubstituted heteroaryl. $R_{33}$ is unsubstituted alkyl, unsubstituted heteroalkyl, unsubstituted cycloalkyl, unsubstituted heterocycloalkyl, unsubstituted aryl, or unsubstituted heteroaryl.

In some embodiments, $R_4$ is independently $R_{31}$-substituted or unsubstituted $C_{1-8}$ alkyl, or $R_{31}$-substituted or unsubstituted $C_{1-8}$ heteroalkyl. In some embodiments, $R_4$ is $R_{31}$-substituted or unsubstituted $C_{1-4}$ alkyl, or $R_{31}$-substituted or unsubstituted $C_{1-4}$ heteroalkyl. In some embodiments, $R_4$ is methyl. In some embodiments, $R_4$ is H.

In some embodiments, the compound with structure of Formula (V) or (VI) has the structure of Formula (Va) or (VIa), respectively, wherein $R_4$ at each occurrence is independently H, or substituted or unsubstituted $C_{1-18}$ alkyl. In some embodiments, $R_4$ at each occurrence is independently unsubstituted $C_{1-8}$ alkyl. In some embodiments, $R_4$ at each occurrence is independently unsubstituted $C_{1-4}$ alkyl. In some embodiments $R_4$ at each occurrence is independently H, $R_{31}$-substituted $C_{1-18}$ alkyl, or $R_{31}$-substituted $C_{1-18}$ heteroalkyl. In some embodiments $R_4$ at each occurrence is independently H, $R_{31}$-substituted $C_{1-8}$ alkyl, or $R_{31}$-substituted $C_{1-8}$ heteroalkyl. In some embodiments $R_4$ at each occurrence is independently H, $R_{31}$-substituted $C_{1-4}$ alkyl, or $R_{31}$-substituted $C_{1-4}$ heteroalkyl. In some embodiments, each $R_4$ is methyl. In some embodiments, the compound has the structure of Formula (Va). In some embodiments, the compound has the structure of Formula (VIa). In some embodiments of Formula (VIa), $R_4$ at each occurrence is H.

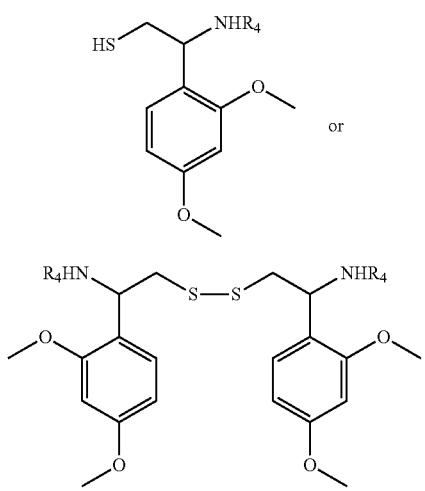

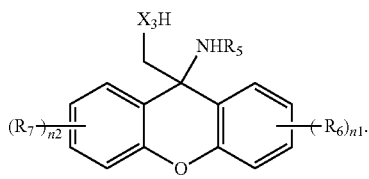

In another aspect, there is provided a compound with structure of Formula (III), wherein $X_3$ is S or Se, $R_5$ is H, substituted or unsubstituted $C_{1-18}$ alkyl, substituted or unsubstituted $C_{1-18}$ heteroalkyl, substituted or unsubstituted $C_{5-14}$ aryl or substituted or unsubstituted $C_{5-14}$ heteroaryl, $R_6$ and $R_7$ are each independently H, cyano, nitro, halo, substituted or unsubstituted $C_{1-18}$ alkyl, substituted or unsubstituted $C_{1-18}$ alkoxy, substituted or unsubstituted $C_{5-14}$ aryl, or substituted or unsubstituted $C_{5-14}$ heteroaryl. n1 and n2 are independently 0-4.

In some embodiments, $R_5$ is H, unsubstituted $C_{1-18}$ alkyl, unsubstituted $C_{1-18}$ heteroalkyl, unsubstituted $C_{5-14}$ aryl or unsubstituted $C_{5-14}$ heteroaryl. $R_6$ and $R_7$ are each independently H, cyano, nitro, halo, unsubstituted $C_{1-18}$ alkyl, unsubstituted $C_{1-18}$ alkoxy, unsubstituted $C_{5-14}$ aryl or unsubstituted $C_{5-14}$ heteroaryl.

In some embodiments, $R_5$ is H, $R_{34}$-substituted $C_{1-18}$ alkyl, $R_{34}$-substituted $C_{1-18}$ heteroalkyl, $R_{34}$-substituted $C_{5-14}$ aryl or $R_{34}$-substituted $C_{5-14}$ heteroaryl. $R_{34}$ is $R_{35}$-substituted or unsubstituted alkyl, $R_{35}$-substituted or unsubstituted heteroalkyl, $R_{35}$-substituted or unsubstituted cycloalkyl, $R_{35}$-substituted or unsubstituted heterocycloalkyl, $R_{35}$-substituted or unsubstituted aryl, or $R_{35}$-substituted or unsubstituted heteroaryl. $R_{35}$ is $R_{36}$-substituted or unsubstituted alkyl, $R_{36}$-substituted or unsubstituted heteroalkyl, $R_{36}$-substituted or unsubstituted cycloalkyl, $R_{36}$-substituted or unsubstituted heterocycloalkyl, $R_{36}$-substituted or unsubstituted aryl, or $R_{36}$-substituted or unsubstituted heteroaryl. $R_{36}$ is unsubstituted alkyl, unsubstituted heteroalkyl, unsubstituted cycloalkyl, unsubstituted heterocycloalkyl, unsubstituted aryl, or unsubstituted heteroaryl. $R_6$ and $R_7$ are each independently H, cyano, nitro, halo, $R_{37}$-substituted $C_{1-18}$ alkyl, $R_{37}$-substituted $C_{1-18}$ alkoxy, $R_{37}$-substituted $C_{5-14}$ aryl or $R_{37}$-substituted $C_{5-14}$ heteroaryl. $R_{37}$ is $R_{38}$-substituted or unsubstituted alkyl, $R_{38}$-substituted or unsubstituted heteroalkyl, $R_{38}$-substituted or unsubstituted cycloalkyl, $R_{38}$-substituted or unsubstituted heterocycloalkyl, $R_{38}$-substituted or unsubstituted aryl, or $R_{38}$-substituted or unsubstituted heteroaryl. $R_{38}$ is $R_{39}$-substituted or unsubstituted alkyl, $R_{39}$-substituted or unsubstituted heteroalkyl, $R_{39}$-substituted or unsubstituted cycloalkyl, $R_{39}$-substituted or unsubstituted heterocycloalkyl, $R_{39}$-substituted or unsubstituted aryl, or $R_{39}$-substituted or unsubstituted heteroaryl. $R_{39}$ is unsubstituted alkyl, unsubstituted heteroalkyl, unsubstituted cycloalkyl, unsubstituted heterocycloalkyl, unsubstituted aryl, or unsubstituted heteroaryl.

In some embodiments of the structures of Formula (III), $R_5$ is H, $R_{34}$-substituted or unsubstituted $C_{1-8}$ alkyl, $R_{34}$-substituted or unsubstituted $C_{1-8}$ heteroalkyl, $R_{34}$-substituted or unsubstituted $C_{6-10}$ aryl, or $R_{34}$-substituted or unsubstituted $C_{6-10}$ heteroaryl. $R_6$ and $R_7$ are independently H, cyano, halo, $R_{37}$-substituted or unsubstituted $C_{1-8}$ alkyl, $R_{37}$-substituted or unsubstituted $C_{1-8}$ heteroalkyl, $R_{37}$-substituted or unsubstituted $C_{1-8}$ alkoxy, $R_{37}$-substituted or unsubstituted $C_{6-10}$ aryl, or $R_{37}$-substituted or unsubstituted $C_{6-10}$ heteroaryl.

In some embodiments of the structures of Formula (III), $R_5$ is H, $R_{34}$-substituted or unsubstituted $C_{1-4}$ alkyl, $R_{34}$-substituted or unsubstituted $C_{1-4}$ heteroalkyl, $R_{34}$-substituted or unsubstituted $C_{6-10}$ aryl, or $R_{34}$-substituted or unsubstituted $C_{6-10}$ heteroaryl. $R_6$ and $R_7$ are independently H, cyano, halo, $R_{37}$-substituted or unsubstituted $C_{1-4}$ alkyl, $R_{37}$-substituted or unsubstituted $C_{1-4}$ heteroalkyl, $R_{37}$-substituted or unsubstituted $C_{1-4}$ alkoxy, $R_{37}$-substituted or unsubstituted $C_{6-10}$ aryl, or $R_{37}$-substituted or unsubstituted $C_{6-10}$ heteroaryl. In some embodiments, $R_6$ and $R_7$ are methoxy.

In still further embodiments of the structures of Formula (III), $R_5$, $R_6$ and $R_7$ are independently selected from any of the above groups or sub-groups, i.e., the groups for $R_5$, $R_6$ and $R_7$ are independently selected as any member from any of the corresponding groups for $R_5$, $R_6$ and $R_7$ disclosed above. Thus, all possible combinations of $R_5$, $R_6$ and $R_7$ disclosed can be used in Formula (III). Also, one or more members can be removed from any of the above disclosed groups or sub-groups of $R_5$, $R_6$ and $R_7$.

In another aspect, there is provided a compound with structure of Formula (VIII). In Formula (VIII), $X_4$ is S or Se. $R_8$ is H, substituted or unsubstituted $C_{1-18}$ alkyl, substituted or unsubstituted $C_{1-18}$ heteroalkyl, substituted or unsubstituted $C_{5-14}$ aryl, or substituted or unsubstituted $C_{5-14}$ heteroaryl. $R_9$ is H, cyano, halo, substituted or unsubstituted $C_{1-18}$ alkyl, substituted or unsubstituted $C_{1-18}$ heteroalkyl, substituted or unsubstituted $C_{1-18}$ alkoxy, substituted or unsubstituted $C_{5-14}$ aryl, or substituted or unsubstituted $C_{5-14}$ heteroaryl. $R_{10}$ at each occurrence is independently H, cyano, nitro, halo, substituted or unsubstituted $C_{1-18}$ alkyl, substituted or unsubstituted $C_{1-18}$ heteroalkyl, substituted or unsubstituted $C_{1-18}$ alkoxy, substituted or unsubstituted $C_{5-14}$ aryl, or substituted or unsubstituted $C_{5-14}$ heteroaryl. p is 0 to 4. In some embodiments, p is 0, 1, 2, 3 or 4.

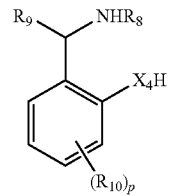

In some embodiments, $R_8$ is H, unsubstituted $C_{1-18}$ alkyl, unsubstituted $C_{1-18}$ heteroalkyl, unsubstituted $C_{5-14}$ aryl, or unsubstituted $C_{5-14}$ heteroaryl. $R_9$ is H, cyano, halo, unsubstituted $C_{1-18}$ alkyl, unsubstituted $C_1$-$C_{18}$ heteroalkyl, unsubstituted $C_{1-18}$ alkoxy, unsubstituted $C_{5-14}$ aryl, or unsubstituted $C_{5-14}$ heteroaryl. $R_{10}$ at each occurrence is independently H, cyano, nitro, halo, unsubstituted $C_{1-18}$ alkyl, unsubstituted $C_{1-18}$ heteroalkyl, unsubstituted $C_{1-18}$ alkoxy, unsubstituted $C_{5-14}$ aryl, or unsubstituted $C_{5-14}$ heteroaryl.

In other embodiments of Formula (VIII), $R_8$ is H, $R_{40}$-substituted $C_{1-18}$ alkyl, $R_{40}$-substituted $C_{1-18}$ heteroalkyl, $R_{40}$-substituted $C_{5-14}$ aryl, or $R_{40}$-substituted $C_{5-14}$ heteroaryl. $R_{40}$ is $R_{41}$-substituted or unsubstituted alkyl, $R_{41}$-substituted or unsubstituted heteroalkyl, $R_{41}$-substituted or unsubstituted cycloalkyl, $R_{41}$-substituted or unsubstituted heterocycloalkyl, $R_{41}$-substituted or unsubstituted aryl, or $R_{41}$-substituted or unsubstituted heteroaryl. $R_{41}$ is $R_{42}$-substituted or unsubstituted alkyl, $R_{42}$-substituted or unsubstituted heteroalkyl, $R_{42}$-substituted or unsubstituted cycloalkyl, $R_{42}$-substituted or unsubstituted heterocycloalkyl, $R_{42}$-substituted or unsubstituted aryl, or $R_{42}$-substituted or unsubstituted heteroaryl. $R_{42}$ is unsubstituted alkyl, unsubstituted heteroalkyl, unsubstituted cycloalkyl, unsubstituted heterocycloalkyl, unsubstituted aryl, or unsubstituted heteroaryl. $R_9$ is H, cyano, halo, $R_{43}$-substituted $C_{1-18}$ alkyl, $R_{43}$-substituted $C_1$-$C_{18}$ heteroalkyl, $R_{43}$-substituted $C_{1-18}$ alkoxy, $R_{43}$-substituted $C_{5-14}$ aryl, or $R_{43}$-substituted $C_{5-14}$ heteroaryl. $R_{43}$ is $R_{44}$-substituted or unsubstituted alkyl, $R_{44}$-substituted or unsubstituted heteroalkyl, $R_{44}$-substituted or unsubstituted cycloalkyl, $R_{44}$-substituted or unsubstituted heterocycloalkyl, $R_{44}$-substituted or unsubstituted aryl, or $R_{44}$-substituted or unsubstituted heteroaryl. $R_{44}$ is $R_{45}$-substituted or unsubstituted alkyl, $R_{45}$-substituted or unsubstituted heteroalkyl, $R_{45}$-substituted or unsubstituted cycloalkyl, $R_{45}$-substituted or unsubstituted heterocycloalkyl, $R_{45}$-substituted or unsubstituted aryl, or $R_{45}$-substituted or unsubstituted heteroaryl. $R_{45}$ is unsubstituted alkyl, unsubstituted heteroalkyl, unsubstituted cycloalkyl, unsubstituted heterocycloalkyl, unsubstituted aryl, or unsubstituted heteroaryl. $R_{10}$ at each occurrence is independently H, cyano, nitro, halo, $R_{46}$-substituted $C_{1-18}$ alkyl, $R_{46}$-substituted $C_{1-18}$ heteroalkyl, $R_{46}$-substituted $C_{1-18}$ alkoxy, $R_{46}$-substituted $C_{5-14}$ aryl, or $R_{46}$-substituted $C_{5-14}$ heteroaryl. $R_{46}$ is $R_{47}$-substituted or unsubstituted alkyl, $R_{47}$-substituted or unsubstituted heteroalkyl, $R_{47}$-substituted or unsubstituted cycloalkyl, $R_{47}$-substituted or unsubstituted heterocycloalkyl, $R_{47}$-substituted or unsubstituted aryl, or $R_{47}$-substituted or unsubstituted heteroaryl. $R_{47}$ is $R_{48}$-substituted or unsubstituted alkyl, $R_{48}$-substituted or unsubstituted heteroalkyl, $R_{48}$-substituted or unsubstituted cycloalkyl, $R_{48}$-substituted or unsubstituted heterocycloalkyl, $R_{48}$-substituted or unsubstituted aryl, or $R_{48}$-substituted or unsubstituted heteroaryl. $R_{48}$ is unsubstituted alkyl, unsubstituted heteroalkyl, unsubstituted cycloalkyl, unsubstituted heterocycloalkyl, unsubstituted aryl, or unsubstituted heteroaryl.

In other embodiments of Formula (VIII), $R_8$ is H, $R_{40}$-substituted or unsubstituted alkyl, $R_{40}$-substituted or unsubstituted $C_{1-8}$ heteroalkyl, $R_{40}$-substituted or unsubstituted $C_{6-10}$ aryl, or $R_{40}$-substituted or unsubstituted $C_{6-10}$ heteroaryl. $R_9$ is H, cyano, halo, $R_{43}$-substituted or unsubstituted $C_{1-8}$ alkyl, $R_{43}$-substituted or unsubstituted $C_1$-$C_8$ heteroalkyl, $R_{43}$-substituted or unsubstituted $C_{1-8}$ alkoxy, $R_{43}$-substituted or unsubstituted $C_{6-10}$ aryl, or $R_{43}$-substituted or unsubstituted $C_{6-10}$ heteroaryl. $R_{10}$ is independently H, cyano, nitro, halo, $R_{46}$-substituted or unsubstituted $C_{1-8}$ alkyl, $R_{46}$-substituted or unsubstituted $C_{1-8}$ heteroalkyl, $R_{46}$-substituted or unsubstituted $C_{1-8}$ alkoxy, $R_{46}$-substituted or unsubstituted $C_{6-10}$ aryl, or $R_{46}$-substituted or unsubstituted $C_{6-19}$ heteroaryl.

In still further embodiments of Formula (VIII), $R_8$ is H, $R_{40}$-substituted or unsubstituted $C_{1-4}$ alkyl, $R_{40}$-substituted or unsubstituted $C_{1-4}$ heteroalkyl, $R_{40}$-substituted or unsubstituted $C_6$ aryl, or $R_{40}$-substituted or unsubstituted $C_6$ heteroaryl. $R_9$ is H, cyano, halo, $R_{43}$-substituted or unsubstituted $C_{1-4}$ alkyl, $R_{43}$-substituted or unsubstituted $C_{1-4}$ heteroalkyl, $R_{43}$-substituted or unsubstituted $C_{1-4}$ alkoxy, $R_{43}$-substituted or unsubstituted $C_6$ aryl, or $R_{43}$-substituted or unsubstituted $C_6$ heteroaryl. $R_{10}$ is independently H, cyano, nitro, halo, $R_{46}$-substituted or unsubstituted $C_{1-4}$ alkyl, $R_{46}$-substituted or unsubstituted $C_{1-4}$ heteroalkyl, $R_{46}$-substituted or unsubstituted $C_{1-4}$ alkoxy, $R_{46}$-substituted or unsubstituted $C_6$ aryl, or $R_{46}$-substituted or unsubstituted $C_6$ heteroaryl. In some embodiments, $R_{10}$ is methoxy.

In other embodiments of Formula (VIII), $R_8$, $R_9$ and $R_{10}$ are independently selected from any of the above groups or sub-groups, i.e., the groups for $R_8$, $R_9$ and $R_{10}$ are independently selected as any member from any of the corresponding groups for $R_8$, $R_9$ and $R_{10}$ disclosed above. Thus, all possible combinations and sub-combinations of $R_8$, $R_9$ and $R_{10}$ disclosed are contemplated for use in Formula (VIII). Also, one or more members can be removed from any of the above disclosed groups or sub-groups of $R_8$, $R_9$ and $R_{10}$.

Specific examples of compounds within Formula (VIII) include Cmpds 81 and 82 having the structures following.

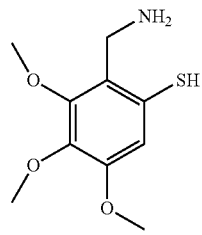

81

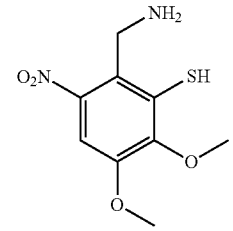

82

In another aspect, there is provided a compound with structure of Formula (IV). In Formula (IV), $R_{11}$ is H, substituted or unsubstituted $C_{1-18}$ alkyl, substituted or unsubstituted $C_{5-14}$ aryl or substituted or unsubstituted $C_{5-14}$ heteroaryl. $R_{12}$ is H, cyano, halo, substituted or unsubstituted $C_{1-18}$ alkyl, substituted or unsubstituted $C_{1-18}$ alkoxy, substituted or unsubstituted $C_{5-14}$ aryl or substituted or unsubstituted $C_{5-14}$ heteroaryl. One of $R_{13}$ and $R_{14}$ is S or Se, and the other is H, cyano, nitro, halo, substituted or unsubstituted $C_{1-18}$ alkyl, substituted or unsubstituted $C_{1-18}$ alkoxy, substituted or unsubstituted $C_{5-14}$ aryl or substituted or unsubstituted $C_{5-14}$ heteroaryl. $R_{15}$ and $R_{16}$ are independently H, cyano, nitro, halo, substituted or unsubstituted $C_{1-18}$ alkyl, substituted or unsubstituted $C_{1-18}$ alkoxy, substituted or unsubstituted $C_{5-14}$ aryl or substituted or unsubstituted $C_{5-14}$ heteroaryl. q1 and q2 are independently 0 to 3.

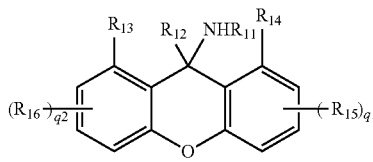

(IV)

In some embodiments, $R_{11}$ is H, unsubstituted $C_{1-18}$ alkyl, unsubstituted $C_{5-14}$ aryl, or unsubstituted $C_{5-14}$ heteroaryl. $R_{12}$ is H, cyano, halo, unsubstituted $C_{1-18}$ alkyl, unsubstituted $C_{1-18}$ alkoxy, unsubstituted $C_{5-14}$ aryl, or unsubstituted $C_{5-14}$ heteroaryl. One of $R_{13}$ and $R_{14}$ is S or Se, and the other is H, cyano, nitro, halo, unsubstituted $C_{1-18}$ alkyl, unsubstituted $C_{1-18}$ alkoxy, unsubstituted $C_{5-14}$ aryl, or unsubstituted $C_{5-14}$ heteroaryl. $R_{15}$ and $R_{16}$ are independently H, cyano, nitro, halo, unsubstituted $C_{1-18}$ alkyl, unsubstituted $C_{1-18}$ alkoxy, unsubstituted $C_{5-14}$ aryl, or unsubstituted $C_{5-14}$ heteroaryl.

In some embodiments, $R_{11}$ is H, $R_{49}$-substituted $C_{1-18}$ alkyl, $R_{49}$-substituted $C_{5-14}$ aryl, or $R_{49}$-substituted $C_{5-14}$ heteroaryl. $R_{49}$ is $R_{50}$-substituted or unsubstituted alkyl, $R_{50}$-substituted or unsubstituted heteroalkyl, $R_{50}$-substituted or unsubstituted cycloalkyl, $R_{50}$-substituted or unsubstituted heterocycloalkyl, $R_{50}$-substituted or unsubstituted aryl, or $R_{50}$-substituted or unsubstituted heteroaryl. $R_{50}$ is $R_{51}$-substituted or unsubstituted alkyl, $R_{51}$-substituted or unsubstituted heteroalkyl, $R_{51}$-substituted or unsubstituted cycloalkyl, $R_{51}$-substituted or unsubstituted heterocycloalkyl, $R_{51}$-substituted or unsubstituted aryl, or $R_{51}$-substituted or unsubstituted heteroaryl. $R_{51}$ is unsubstituted alkyl, unsubstituted heteroalkyl, unsubstituted cycloalkyl, unsubstituted heterocycloalkyl, unsubstituted aryl, or unsubstituted heteroaryl. $R_{12}$ is H, cyano, halo, $R_{52}$-substituted $C_{1-18}$ alkyl, $R_{52}$-substituted $C_{1-18}$ alkoxy, $R_{52}$-substituted $C_{5-14}$ aryl, or $R_{52}$-substituted $C_{5-14}$ heteroaryl. $R_{52}$ is $R_{53}$-substituted or unsubstituted alkyl, $R_{53}$-substituted or unsubstituted heteroalkyl, $R_{53}$-substituted or unsubstituted cycloalkyl, $R_{53}$-substituted or unsubstituted heterocycloalkyl, $R_{53}$-substituted or unsubstituted aryl, or $R_{53}$-substituted or unsubstituted heteroaryl. $R_{53}$ is $R_{54}$-substituted or unsubstituted alkyl, $R_{54}$-substituted or unsubstituted heteroalkyl, $R_{54}$-substituted or unsubstituted cycloalkyl, $R_{54}$-substituted or unsubstituted heterocycloalkyl, $R_{54}$-substituted or unsubstituted aryl, or $R_{54}$-substituted or unsubstituted heteroaryl. $R_{54}$ is unsubstituted alkyl, unsubstituted heteroalkyl, unsubstituted cycloalkyl, unsubstituted heterocycloalkyl, unsubstituted aryl, or unsubstituted heteroaryl. One of $R_{13}$ and $R_{14}$ is S or Se, and the other is H, cyano, nitro, halo, $R_{55}$-substituted $C_{1-18}$ alkyl, $R_{55}$-substituted $C_{1-18}$ alkoxy, $R_{55}$-substituted $C_{5-14}$ aryl, or $R_{55}$-substituted $C_{5-14}$ heteroaryl. $R_{55}$ is $R_{56}$-substituted or unsubstituted alkyl, $R_{56}$-substituted or unsubstituted heteroalkyl, $R_{56}$-substituted or unsubstituted cycloalkyl, $R_{56}$-substituted or unsubstituted heterocycloalkyl, $R_{56}$-substituted or unsubstituted aryl, or $R_{56}$-substituted or unsubstituted heteroaryl. $R_{56}$ is $R_{57}$-substituted or unsubstituted alkyl, $R_{57}$-substituted or unsubstituted heteroalkyl, $R_{57}$-substituted or unsubstituted cycloalkyl, $R_{57}$-substituted or unsubstituted heterocycloalkyl, $R_{57}$-substituted or unsubstituted aryl, or $R_{57}$-substituted or unsubstituted heteroaryl. $R_{57}$ is unsubstituted alkyl, unsubstituted heteroalkyl, unsubstituted cycloalkyl, unsubstituted heterocycloalkyl, unsubstituted aryl, or unsubstituted heteroaryl. $R_{15}$ and $R_{16}$ are independently H, cyano, nitro, halo, $R_{58}$-substituted $C_{1-18}$ alkyl, $R_{58}$-substituted $C_{1-18}$ alkoxy, $R_{58}$-substituted $C_{5-14}$ aryl, or $R_{58}$-substituted $C_{5-14}$ heteroaryl. $R_{58}$ is $R_{59}$-substituted or unsubstituted alkyl, $R_{59}$-substituted or unsubstituted heteroalkyl, $R_{59}$-substituted or unsubstituted cycloalkyl, $R_{59}$-substituted or unsubstituted heterocycloalkyl, $R_{59}$-substituted or unsubstituted aryl, or $R_{59}$-substituted or unsubstituted heteroaryl. $R_{59}$ is $R_{60}$-substituted or unsubstituted alkyl, $R_{60}$-substituted or unsubstituted heteroalkyl, $R_{60}$-substituted or unsubstituted cycloalkyl, $R_{60}$-substituted or unsubstituted heterocycloalkyl, $R_{60}$-substituted or unsubstituted aryl, or $R_{60}$-substituted or unsubstituted heteroaryl. $R_{60}$ is unsubstituted alkyl, unsubstituted heteroalkyl, unsubstituted cycloalkyl, unsubstituted heterocycloalkyl, unsubstituted aryl, or unsubstituted heteroaryl.

In some embodiments, $R_{11}$ is $R_{49}$-substituted $C_{1-8}$ alkyl, $R_{49}$-substituted $C_{5-14}$ aryl, or $R_{49}$-substituted $C_{5-14}$ heteroaryl. $R_{12}$ is H, cyano, halo, $R_{52}$-substituted $C_{1-8}$ alkyl, $R_{52}$-substituted $C_{1-8}$ alkoxy, $R_{52}$-substituted $C_{5-14}$ aryl, or $R_{52}$-substituted $C_{5-14}$ heteroaryl. One of $R_{13}$ and $R_{14}$ is S or Se, and the other is H, cyano, nitro, halo, $R_{55}$-substituted $C_{1-8}$ alkyl, $R_{55}$-substituted $C_{1-8}$ alkoxy, $R_{55}$-substituted $C_{5-14}$ aryl, or $R_{55}$-substituted $C_{5-14}$ heteroaryl. $R_{15}$ and $R_{16}$ are independently H, cyano, nitro, halo, $R_{58}$-substituted $C_{1-8}$ alkyl, $R_{58}$-substituted $C_{1-8}$ alkoxy, $R_{58}$-substituted $C_{5-14}$ aryl, or $R_{58}$-substituted $C_{5-14}$ heteroaryl.

In some embodiments, $R_{11}$ is $R_{49}$-substituted $C_{1-4}$ alkyl, $R_{49}$-substituted $C_{5-14}$ aryl, or $R_{49}$-substituted $C_{5-14}$ heteroaryl. $R_{12}$ is H, cyano, halo, $R_{52}$-substituted $C_{1-4}$ alkyl, $R_{52}$-substituted $C_{1-4}$ alkoxy, $R_{52}$-substituted $C_{5-14}$ aryl, or $R_{52}$-substituted $C_{5-14}$ heteroaryl. One of $R_{13}$ and $R_{14}$ is S or Se, and the other is H, cyano, nitro, halo, $R_{55}$-substituted $C_{1-4}$ alkyl, $R_{55}$-substituted $C_{1-4}$ alkoxy, $R_{55}$-substituted $C_{5-14}$ aryl, or $R_{55}$-substituted $C_{5-14}$ heteroaryl. $R_{15}$ and $R_{16}$ are independently H, cyano, nitro, halo, $R_{58}$-substituted $C_{1-4}$ alkyl, $R_{58}$-substituted $C_{1-8}$ alkoxy, $R_{58}$-substituted $C_{5-14}$ aryl, or $R_{58}$-substituted $C_{5-14}$ heteroaryl.

In another aspect, there is provided a polypeptide adduct with structure of Formula 10 or Formula 11 following, wherein the term "PP" is a polypeptide described herein or known in the art. The polypeptide adduct is formed by bonding at the C-terminus of the polypeptide. In some embodiments, the polypeptide comprises 2 to 200 residues.

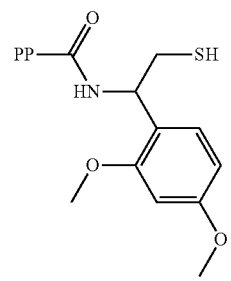

10

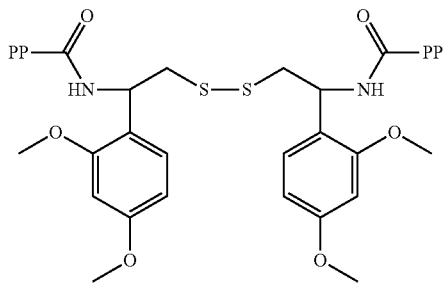

Also disclosed are compounds of Formula 12 following, wherein PP is as defined for Formulae 10-11.

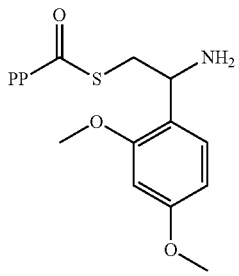

III. Methods of Use

In another aspect, there is provided a method for producing a C-terminal free amide polypeptide. The method includes contacting a C-terminal thioester polypeptide with an auxiliary molecule which is a substituted or unsubstituted 2-phenyl-2-amino ethanethiol, thereby forming a C-terminal substituted amide polypeptide substituted with a 2-phenyl-2-amino ethanethiol moiety, or contacting a C-terminal selenoester polypeptide with an auxiliary molecule which is a substituted or unsubstituted 2-phenyl-2-amino ethaneselenol, thereby forming a C-terminal substituted amide polypeptide substituted with a 2-phenyl-2-amino ethaneselenol moiety. In a subsequent step, the 2-phenyl-2-amino ethanethiol moiety or 2-phenyl-2-amino ethaneselenol moiety is removed, thereby forming the C-terminal free amide polypeptide.

In some embodiments, a C-terminal thioester polypeptide is contacted with a substituted or unsubstituted 2-phenyl-2-amino ethanethiol. In some embodiments, a C-terminal selenoester polypeptide is contacted with a substituted or unsubstituted 2-phenyl-2-amino ethaneselenol. In some embodiments, the 2-phenyl-2-amino ethanethiol moiety is removed, thereby forming the C-terminal free amide polypeptide. In some embodiments, the 2-phenyl-2-amino ethaneselenol moiety is removed, thereby forming the C-terminal free amide polypeptide.

As used herein, the term "moiety" in the context of a non-peptidic compound refers to a component of a polypeptide adduct formed during a method described herein. The terms "polypeptide adduct" and the like refer to a chemical addition compound formed by the chemical addition of an auxiliary molecule, or portion thereof, with a C-terminal thioester polypeptide or C-terminal selenoester polypeptide. Exemplary polypeptide adducts include, for example, a C-terminal substituted amide polypeptide substituted with a 2-phenyl-2-amino ethanethiol moiety, a C-terminal substituted amide polypeptide substituted with a 2-phenyl-2-amino ethaneselenol moiety, and a C-terminal substituted amide polypeptide substituted with a substituted xanthene moiety. "Auxiliary molecule" refers to a compound which can form a thioester or selenoester bond to a polypeptide described herein, thereby forming a polypeptide adduct. It is understood that thioester and/or selenoester bond formation may result in the loss of an atom or group, e.g., a proton, from the auxiliary molecule and/or the C-terminal of the polypeptide. Exemplary auxiliary molecules include compounds having the structure of Formulae (I), (III), (IV) or (VIII). The polypeptide and the auxiliary molecule forming the polypeptide adduct are chemically bonded by at least one covalent bond. The "moiety" of the auxiliary molecule is that portion of the polypeptide adduct that is derived from the auxiliary molecule. Exemplary moieties of polypeptide adducts described herein include, for example, a 2-phenyl-2-amino ethanethiol moiety, 2-phenyl-2-amino ethaneselenol moiety, a substituted xanthene moiety, and the like as described herein.

Further to any aspect or embodiment described herein, it is understood that a polypeptide adduct may undergo chemical transformation, for example N—S acyl shift, N—O acyl shift, trans-esterification and/or trans-thioesterification, during the course of amidation of the C-terminus of the polypeptide by a method described herein. Accordingly, the terms "removing a moiety" (e.g., 2-phenyl-2-amino ethanethiol moiety or 2-phenyl-2-amino ethaneselenol moiety, substituted xanthene moiety) and like refer to chemical bond cleavage which results in a polypeptide having an amidated C-terminus, irrespective of any chemical changes which the auxiliary molecule or the polypeptide undergo while forming the polypeptide adduct. It is understood that one or more protons may add during bond cleavage as described herein.

In some embodiments, the substituted or unsubstituted 2-phenyl-2-amino ethanethiol or substituted or unsubstituted 2-phenyl-2-amino ethaneselenol useful in the method has the structure of Formula (I), wherein $R_1$, $R_2$, $R_3$, $X_1$ and m are as defined above for Formula (I).

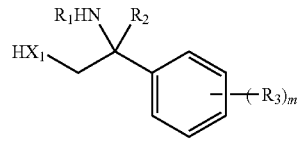

In some embodiments, the auxiliary molecule includes a 2,4-disubstituted phenyl functionality. In some embodiments, the 2,4-disubstituted phenyl functionality is independently substituted with O-methyl, S-methyl, N-methyl, or substituted amine. In some embodiments, the 2,4-disubstituted phenyl functionality is independently substituted with O-methyl, S-methyl, N-methyl, or nitro.

In some embodiments, the polypeptide includes a C-terminal thioester, and the auxiliary molecule has the structure of Cmpd 4 or Cmpd 5 following.

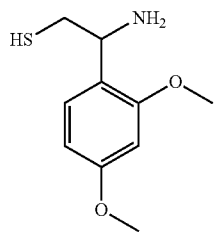

4

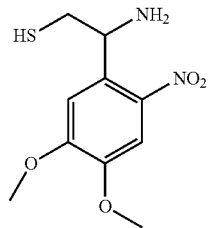

5

In another aspect, there is provided a method for producing a C-terminus free amide polypeptide. In a first step, a polypeptide which includes a C-terminal thioester or C-terminal selenoester is contacted with a compound having the structure of Formula (III) under conditions suitable to produce a polypeptide adduct wherein a moiety derived from the compound having the structure of Formula (III) is bonded at the C-terminal of the polypeptide (i.e., a C-terminal substituted amide polypeptide substituted with a substituted xanthene moiety). For Formula (III), $R_5$, $R_6$, $R_7$, $X_3$, n1 and n2 are as defined above for the compound having the structure of Formula (III).

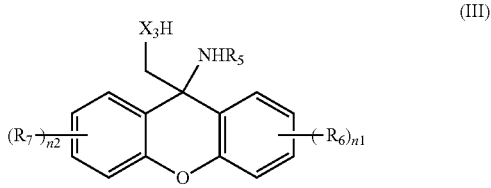

In a subsequent step, the substituted xanthene moiety is removed from the C-terminal substituted amide polypeptide substituted with a substituted xanthene moiety, thereby forming a C-terminal free amide polypeptide.

In some embodiments, a C-terminal thioester polypeptide is contacted in the first step with a compound of Formula (III) wherein $X_3$ is S. In some embodiments, a C-terminal selenoester polypeptide is contacted in the first step with a compound of Formula (III) wherein $X_3$ is Se.

In some embodiments of the structures of Formula (III) useful in the method, $R_5$ is H, substituted or unsubstituted $C_{1-18}$ alkyl, substituted or unsubstituted $C_{1-18}$ heteroalkyl, substituted or unsubstituted $C_{5-14}$ aryl, or substituted or unsubstituted $C_{5-14}$ heteroaryl. $R_6$ and $R_7$ are independently H, cyano, halo, substituted or unsubstituted $C_{1-18}$ alkyl, substituted or unsubstituted $C_{1-18}$ heteroalkyl, substituted or unsubstituted $C_{1-18}$ alkoxy, substituted or unsubstituted $C_{5-14}$ aryl, or substituted or unsubstituted $C_{4-15}$ heteroaryl.

In some embodiments, $R_5$ is H, substituted or unsubstituted $C_{1-8}$ alkyl, substituted or unsubstituted $C_{1-8}$ heteroalkyl, substituted or unsubstituted $C_{6-10}$ aryl, or substituted or unsubstituted $C_{6-10}$ heteroaryl. $R_6$ and $R_7$ are independently H, cyano, halo, substituted or unsubstituted $C_{1-8}$ alkyl, substituted or unsubstituted $C_{1-8}$ heteroalkyl, substituted or unsubstituted $C_{1-8}$ alkoxy, substituted or unsubstituted $C_{6-10}$ aryl, or substituted or unsubstituted $C_{6-10}$ heteroaryl.

In further embodiments, $R_5$ is H, substituted or unsubstituted $C_{1-4}$ alkyl, substituted or unsubstituted $C_{1-4}$ heteroalkyl, substituted or unsubstituted $C_6$ aryl, or substituted or unsubstituted $C_6$ heteroaryl. $R_6$ and $R_7$ independently H, cyano, halo, substituted or unsubstituted $C_{1-4}$ alkyl, substituted or unsubstituted $C_{1-4}$ heteroalkyl, substituted or unsubstituted $C_{1-4}$ alkoxy, substituted or unsubstituted $C_6$ aryl, or substituted or unsubstituted $C_6$ heteroaryl.

In still further embodiments, $R_5$, $R_6$ and $R_7$ are independently selected from any of the above groups or sub-groups, i.e., the groups for $R_5$, $R_6$ and $R_7$ are independently selected as any member from any of the corresponding groups for $R_5$, $R_6$ and $R_7$ disclosed above. Thus, all possible combinations of $R_5$, $R_6$ and $R_7$ disclosed can be used in Formula (III). Also, one or more members can be removed from any of the above disclosed groups or sub-groups of $R_5$, $R_6$ and $R_7$.

In one embodiment, the compound having the structure of Formula (III) has the structure of Cmpd 6 following.

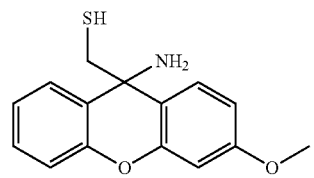

In another aspect, there is provided a method for producing a C-terminal free amide polypeptide by contacting, in a first step, a C-terminal thioester polypeptide or a C-terminal selenoester polypeptide with a thiol or selenoester auxiliary molecule having the structure of Formula (IV) to produce a C-terminal substituted amide polypeptide substituted with a substituted xanthene moiety. In the compound having the structure of Formula (IV), $R_{11}$, $R_{12}$, $R_{13}$, $R_{14}$, $R_{15}$, $R_{16}$, q1 and q2 are as defined above for the compound having the structure of Formula (IV).

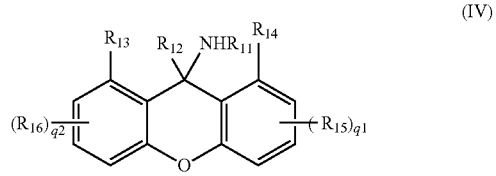

In a subsequent step, the substituted xanthene moiety is removed, thereby forming a C-terminal free amide polypeptide. In some embodiments, when a C-terminal thioester polypeptide is contacted, then $R_{13}$ or $R_{14}$ is S, and when a C-terminal selenoester polypeptide is contacted, then $R_{13}$ or $R_{14}$ is Se.

In some embodiments of Formula (IV) useful in the method, $R_{11}$ is H, substituted or unsubstituted $C_{1-18}$ alkyl, substituted or unsubstituted $C_{1-18}$ heteroalkyl, substituted or unsubstituted $C_{5-14}$ aryl, or substituted or unsubstituted $C_{5-14}$ heteroaryl. $R_{12}$ is H, cyano, halo, substituted or unsubstituted $C_{1-18}$ alkyl, substituted or unsubstituted $C_{1-18}$ heteroalkyl, substituted or unsubstituted $C_{1-8}$ alkoxy, substituted or unsubstituted $C_{5-14}$ aryl, or substituted or unsubstituted $C_{5-14}$ heteroaryl. One of $R_{13}$ and $R_{14}$ is S or Se, and the other is H, cyano, nitro, halo, substituted or unsubstituted $C_{1-18}$ alkyl, substituted or unsubstituted $C_{1-18}$ heteroalkyl, substituted or unsubstituted $C_{1-18}$ alkoxy, substituted or unsubstituted $C_{5-14}$ aryl, or substituted or unsubstituted $C_{5-14}$ heteroaryl. $R_7$ and $R_8$ are independently selected from, cyano, nitro, halo, substituted or unsubstituted $C_{1-18}$ alkyl, substituted or unsubstituted $C_{1-18}$ heteroalkyl, substituted or unsubstituted $C_{1-18}$ alkoxy, substituted or unsubstituted $C_{5-14}$ aryl, or substituted or unsubstituted $C_{5-14}$ heteroaryl.

In some embodiments, $R_{11}$ is H, substituted or unsubstituted $C_{1-8}$ alkyl, substituted or unsubstituted $C_{1-8}$ heteroalkyl, substituted or unsubstituted $C_{6-10}$ aryl, or substituted or unsubstituted $C_{6-10}$ heteroaryl. $R_{12}$ is H, cyano, halo, substituted or unsubstituted $C_{1-8}$ alkyl, substituted or unsubstituted $C_{1-8}$ heteroalkyl, substituted or unsubstituted $C_{1-8}$ alkoxy, substituted or unsubstituted $C_{6-10}$ aryl, or substituted or unsubstituted $C_{6-10}$ heteroaryl. One of $R_{13}$ and $R_{14}$ is S or Se, and the other is H, cyano, nitro, halo, substituted or unsubstituted $C_{1-8}$ alkyl, substituted or unsubstituted $C_{1-8}$ heteroalkyl, substituted or unsubstituted $C_{1-8}$ alkoxy, substituted or unsubstituted $C_{6-10}$ aryl, or substituted or unsubstituted $C_{6-10}$ heteroaryl. $R_7$ and $R_8$ are independently selected from, cyano, nitro, halo, substituted or unsubstituted $C_{1-8}$ alkyl, substituted or unsubstituted $C_{1-8}$ heteroalkyl, substituted or unsubstituted $C_{1-8}$ alkoxy, substituted or unsubstituted $C_{6-10}$ aryl, or substituted or unsubstituted $C_{6-10}$ heteroaryl.

In further embodiments, $R_{11}$ is H, substituted or unsubstituted $C_{1-4}$ alkyl, substituted or unsubstituted $C_{1-4}$ heteroalkyl, substituted or unsubstituted $C_6$ aryl, or substituted or unsubstituted $C_6$ heteroaryl. $R_{12}$ is H, cyano, halo, substituted or unsubstituted $C_{1-4}$ alkyl, substituted or unsubstituted $C_{1-4}$ heteroalkyl, substituted or unsubstituted $C_{1-4}$ alkoxy, substituted or unsubstituted $C_6$ aryl, or substituted or unsubstituted $C_6$ heteroaryl. One of $R_{13}$ and $R_{14}$ is S or Se, and the other is H, cyano, nitro, halo, substituted or unsubstituted $C_{1-4}$ alkyl, substituted or unsubstituted $C_{1-4}$ heteroalkyl, substituted or unsubstituted $C_{1-4}$ alkoxy, substituted or unsubstituted $C_6$ aryl, or substituted or unsubstituted $C_6$ heteroaryl. $R_{15}$ and $R_{16}$ are independently H, cyano, nitro, halo, substituted or unsubstituted $C_{1-4}$ alkyl, substituted or unsubstituted $C_{1-4}$ heteroalkyl, substituted or unsubstituted $C_{1-4}$ alkoxy, substituted or unsubstituted $C_6$ aryl, or substituted or unsubstituted $C_6$ heteroaryl.

In other embodiments of Formula (IV), $R_{11}$, $R_{12}$, $R_{15}$, and $R_{16}$ are independently selected from any of the above groups or sub-groups, i.e., the groups for $R_{11}$, $R_{12}$, $R_{15}$ and $R_{16}$ are independently selected as any member from any of the corresponding groups for $R_{11}$, $R_{12}$, $R_{12}$ and $R_{16}$ disclosed above. Thus, all possible combinations of $R_{11}$, $R_{12}$, $R_{15}$ and $R_{16}$ disclosed can be used. Also, one or more members can be removed from any of the above disclosed groups or sub-groups of $R_{11}$, $R_{12}$, $R_{15}$ and $R_{16}$.

In one embodiment the compound of Formula (IV) has the structure of Cmpd 7 following:

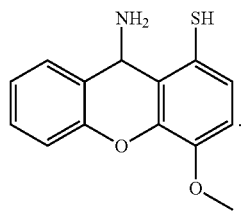

7

In another aspect, there is provided a method for producing a C-terminal free amide polypeptide. In a first step, a polypeptide which includes a C-terminal thioester or C-terminal selenoester is contacted with an auxiliary molecule under conditions suitable to produce a polypeptide adduct, wherein the auxiliary molecule is bonded at the C-terminal of the polypeptide. The polypeptide adduct is a C-terminal substituted amide polypeptide substituted with a substituted or unsubstituted aminomethyl thiophenol moiety or substituted or unsubstituted aminomethyl selenophenol moiety. The auxiliary molecule has the structure of Formula (VIII), wherein $R_8$, $R_9$, $R_{10}$, $X_4$, and p are as defined above for the compound having the structure of Formula (VIII).

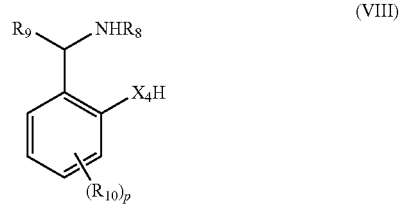

(VIII)

In a subsequent step, the substituted or unsubstituted aminomethyl thiophenol moiety or substituted or unsubstituted aminomethyl selenophenol moiety is removed from the C-terminal of the polypeptide adduct under conditions suitable to produce C-terminal free amide polypeptide.

In some embodiments of the method, $R_8$ is H, substituted or unsubstituted $C_{1-18}$ alkyl, substituted or unsubstituted $C_{1-18}$ heteroalkyl, substituted or unsubstituted $C_{5-14}$ aryl, or substituted or unsubstituted $C_{5-14}$ heteroaryl. $R_9$ is H, cyano, halo, substituted or unsubstituted $C_{1-18}$ alkyl, substituted or unsubstituted $C_1$-$C_{18}$ heteroalkyl, substituted or unsubstituted $C_{1-18}$ alkoxy, substituted or unsubstituted $C_{5-14}$ aryl, or substituted or unsubstituted $C_{5-14}$ heteroaryl. $R_{10}$ is independently H, cyano, nitro, halo, substituted or unsubstituted $C_{1-18}$ alkyl, substituted or unsubstituted $C_{1-18}$ heteroalkyl, substituted or unsubstituted $C_{1-18}$ alkoxy, substituted or unsubstituted $C_{5-14}$ aryl, or substituted or unsubstituted $C_{5-14}$ heteroaryl.

In some embodiments, $R_8$ is H, substituted or unsubstituted $C_{1-8}$ alkyl, substituted or unsubstituted $C_{1-8}$ heteroalkyl, substituted or unsubstituted $C_{6-10}$ aryl, or substituted or unsubstituted $C_{6-10}$ heteroaryl. $R_9$ is H, cyano, halo, substituted or unsubstituted $C_{1-8}$ alkyl, substituted or unsubstituted $C_1$-$C_8$ heteroalkyl, substituted or unsubstituted $C_{1-8}$ alkoxy, substituted or unsubstituted $C_{6-10}$ aryl, or substituted or unsubstituted $C_{6-10}$ heteroaryl. $R_{10}$ is independently H, cyano, nitro, halo, substituted or unsubstituted $C_{1-8}$ alkyl, substituted or unsubstituted $C_{1-8}$ heteroalkyl, substituted or unsubstituted $C_{1-8}$ alkoxy, substituted or unsubstituted $C_{6-10}$ aryl, or substituted or unsubstituted $C_{6-10}$ heteroaryl.

In further embodiments, $R_8$ is H, substituted or unsubstituted $C_{1-4}$ alkyl, substituted or unsubstituted $C_{1-4}$ heteroalkyl, substituted or unsubstituted $C_6$ aryl, or substituted or unsubstituted $C_6$ heteroaryl. $R_9$ is H, cyano, halo, substituted or unsubstituted $C_{1-4}$ alkyl, substituted or unsubstituted $C_{1-4}$ heteroalkyl, substituted or unsubstituted $C_{1-4}$ alkoxy, substituted or unsubstituted $C_6$ aryl, or substituted or unsubstituted $C_6$ heteroaryl. $R_{10}$ is independently H, cyano, nitro, halo, substituted or unsubstituted $C_{1-4}$ alkyl, substituted or unsubstituted $C_{1-4}$ heteroalkyl, substituted or unsubstituted $C_{1-4}$ alkoxy, substituted or unsubstituted $C_6$ aryl, or substituted or unsubstituted $C_6$ heteroaryl.

In other embodiments, $R_8$, $R_9$ and $R_{10}$ are independently selected from any of the above groups or sub-groups, i.e., the groups for $R_8$, $R_9$ and $R_{10}$ are independently selected as any member from any of the corresponding groups for $R_8$, $R_9$ and $R_{10}$ disclosed above. Thus, all possible combinations and sub-combinations of $R_8$, $R_9$ and $R_{10}$ disclosed are contemplated for use in Formula (VIII). Also, one or more members can be removed from any of the above disclosed groups or sub-groups of $R_8$, $R_9$ and $R_{10}$.

Specific examples of compounds with structure of Formula (VIII) useful in the method include Cmpds 81 and 82 having the structures following.

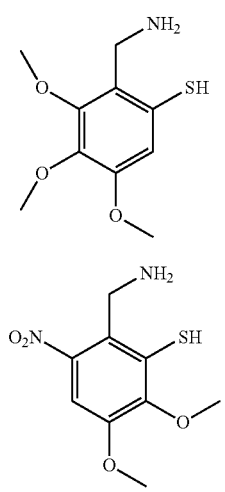

Cmpd 81 can be cleaved with 95% TFA. Cmpd 82 is photocleavable. Either compound is useful according to methods herein where such conditions can be used.

Further to any of the methods disclosed herein for producing a C-terminal free amide polypeptide, in some embodiments the substituted or unsubstituted 2-phenyl-2-amino ethanethiol moiety, substituted or unsubstituted 2-phenyl-2-amino ethaneselenol moiety, substituted xanthene moiety, substituted or unsubstituted aminomethyl thiophenol moiety or substituted or unsubstituted aminomethyl selenophenol moiety is removed from the C-terminus of the polypeptide by reaction with acid. Exemplary acids include trifluoroacetic acid and trifluoromethanesulfonic acid. In some embodiments, the acid is a weak acid. In some embodiments, the acid is acetic acid, citric acid, boric acid, phosphoric acid, or hydrofluoric acid. The acid can be a solid support, such as an acidic catalyst resin, as known in the art. In some embodiments, the moiety derived from the auxiliary molecule can be removed from the C-terminus of the polypeptide by exposure to light rays.

There are provided generally facile chemical method of amidation with a high conversion rate. The reactions can be performed under mild conditions and are thus advantageous over other chemical methods of amidation which employ less mild conditions. In some embodiments, a method described herein is performed at pH between 5 and 9, or between 6.5 and 8.5.

The disclosed methods offer distinct advantages over previous methods. In one embodiment the conversion rate of polypeptides containing a C-terminal thioester or selenoester into amidated polypeptides is at least 40%, e.g., 40%, 50%, 60%, 70%, 80%, 90%, 95% or even larger. In other embodiments the conversion rate is from 40% to 70%, or from about 50% to about 80% of a polypeptide containing a C-terminal thioester or selenoester converted into amidated polypeptide. In still further embodiments of the methods conversion rates of at least 85% or at least 90% or at least 95% are achieved.

In some embodiments, a C-terminal thioester polypeptide or a C-terminal selenoester polypeptide is converted into a C-terminal free amide polypeptide at a rate of at least 40%.

Further to any of the methods disclosed herein for producing a C-terminal free amide polypeptide, in some embodiments the C-terminal thioester polypeptide or the C-terminal selenoester polypeptide includes two or more amino acids, e.g., 25 or more amino acids, 50 or more amino acids, 100 or more amino acids, or even 200 or more amino acids.

Further to any of the methods disclosed herein for producing a C-terminal free amide polypeptide, in some embodiments the C-terminal thioester polypeptide or C-terminal selenoester polypeptide includes a polypeptide moiety which is a pramlintide moiety, exendin-4 moiety, davalintide moiety, glucagon-like peptide-1 (7-37) [GLP-1(7-37)] moiety, meterleptin moiety, peptide-YY (3-36) [PYY(3-36)] moiety, gastric inhibitory polypeptide (GIP) moiety, insulin moiety, human growth hormone (HGH) moiety, erythropoietin (EPO) moiety, cholecystokinin (CCK) moiety, glucagon-like peptide-1 (GLP-2) moiety, GLP-1/glucagon chimeric peptide moiety, GLP-1/GIP chimeric peptide moiety, neurotensin moiety, urocortin moiety, neuromedin moiety, hybrid thereof or analog thereof. In some embodiments, the C-terminal thioester polypeptide or C-terminal selenoester polypeptide contains one polypeptide moiety as disclosed above. In some embodiments, the C-terminal thioester polypeptide or C-terminal selenoester polypeptide contains one or more polypeptide moieties as disclosed above. The term "moiety" in the context of a polypeptide refers to a polypeptide combined to form a polypeptide adduct as defined herein.

Further to any of Formulae (I)-(VIII), in some embodiments a substituent is a size-limited substituent. For example without limitation, in some embodiments each substituted or unsubstituted alkyl may be a substituted or unsubstituted $C_1$-$C_{18}$, $C_1$-$C_8$, $C_1$-$C_4$, or even $C_1$ alkyl. In some embodiments each substituted or unsubstituted heteroalkyl may be a substituted or unsubstituted 2-18 membered, 2-8 membered, or 2-4 membered heteroalkyl. In some embodiments, each substituted or unsubstituted heteroaryl is a substituted or unsubstituted 4-14 membered, 5-15 membered, 4-10 membered, 5-10 membered, 5-8 membered, 4-6 membered, 5-6 membered, 6-membered heteroaryl, or 5-membered heteroaryl. In some embodiments, each substituted or unsubstituted aryl is a substituted or unsubstituted $C_4$-$C_{18}$, $C_5$-$C_{14}$, $C_4$-$C_{14}$, $C_4$-$C_{10}$, $C_5$-$C_{10}$, $C_6$-$C_{10}$, $C_5$-$C_8$, $C_5$-$C_6$, or $C_6$ aryl.

IV. Reactions

With reference to the general chemical schemes disclosed herein and depicted, e.g., in Scheme 1 following, Cmpd 4 (2-amino-2-(2,4-dimethoxyphenyl)ethanethiol) is an auxiliary molecule that contacts polypeptide thioester 101 under suitable conditions to generate the polypeptide adduct 104, wherein the auxiliary molecule is bonded at the C-terminus of the polypeptide. In Scheme 1, the polypeptide adduct is a C-terminal substituted amide polypeptide substituted with a 2-phenyl-2-amino ethanethiol moiety. The 2-phenyl-2-amino ethanethiol moiety is the —NHCH(CH₂SH)-phenyl (OCH₃)₂, depicted in Scheme 1 as part of Cmpd 104. Upon treatment with a suitable acid, e.g., trifluoro acetic acid (TFA), the polypeptide amide product 106 is produced, and the moiety derived from the auxiliary molecule, or a portion thereof, is removed.

Removing the moiety of the auxiliary molecule can also indicate removing a portion of the moiety and leaving, for example, the amide nitrogen, to produce the amidated polypeptide. The polypeptide thioester 101 (which can also be a selenoester) can be produced through protein expression, as known in the art, in which, for example, protein is fused to the N-terminus of an intein.

In some embodiments, the polypeptide to be amidated includes an intein. As known in the art, the term "intein" refers to a segment of a polypeptide that is able to be excised with rejoinder of the remaining portion with a peptide bond. See e.g., Anraka et al., 2005, *IUBMB Life* 57:563-574. Under certain conditions, the peptide-intein fusion protein can undergo a thiol-mediated self cleavage to form the peptide thioester 101. Further any aspect or embodiment disclosed herein, the auxiliary molecule can also initially be present in a dimerized form (e.g., Cmpd 15), and cleaved to produce the monomer form Cmpd 4.

Scheme 1

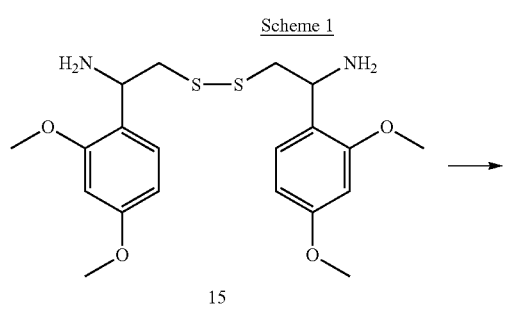

15

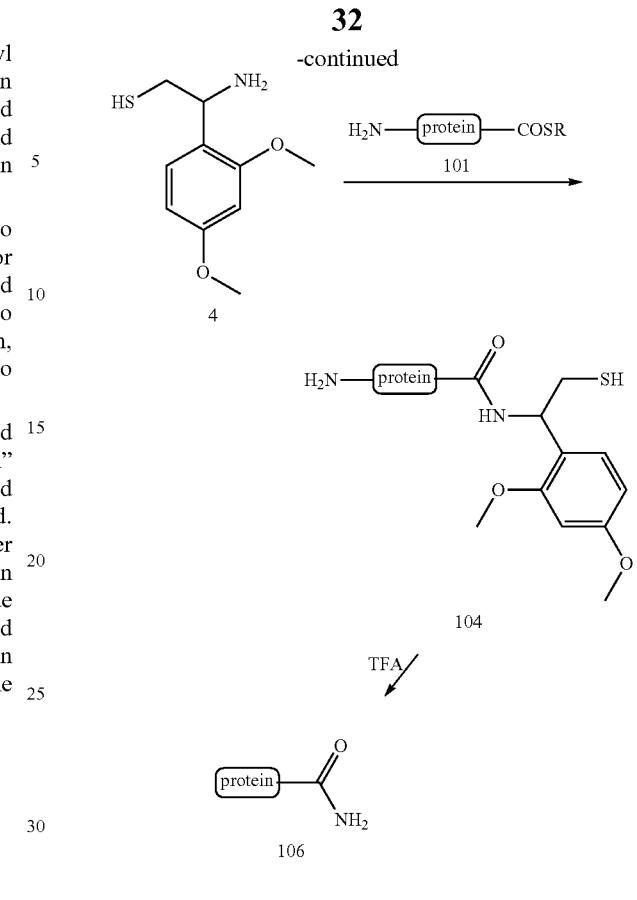

An exemplary outline of a chemical mechanism is provided in Scheme 4 following. Regarding Scheme 4, the term "Peptide" represents a generic polypeptide (e.g., any of those described herein or known in the art) that is to be amidated at the C-terminal. The specific polypeptide used in the invention is not crucial, as persons of ordinary skill in the art with reference to this disclosure will understand that the methods are applicable to a broad range of polypeptides.

Scheme 4

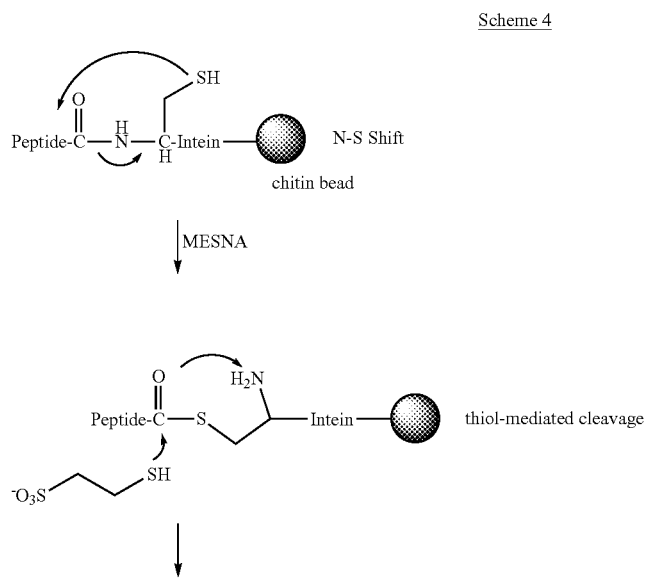

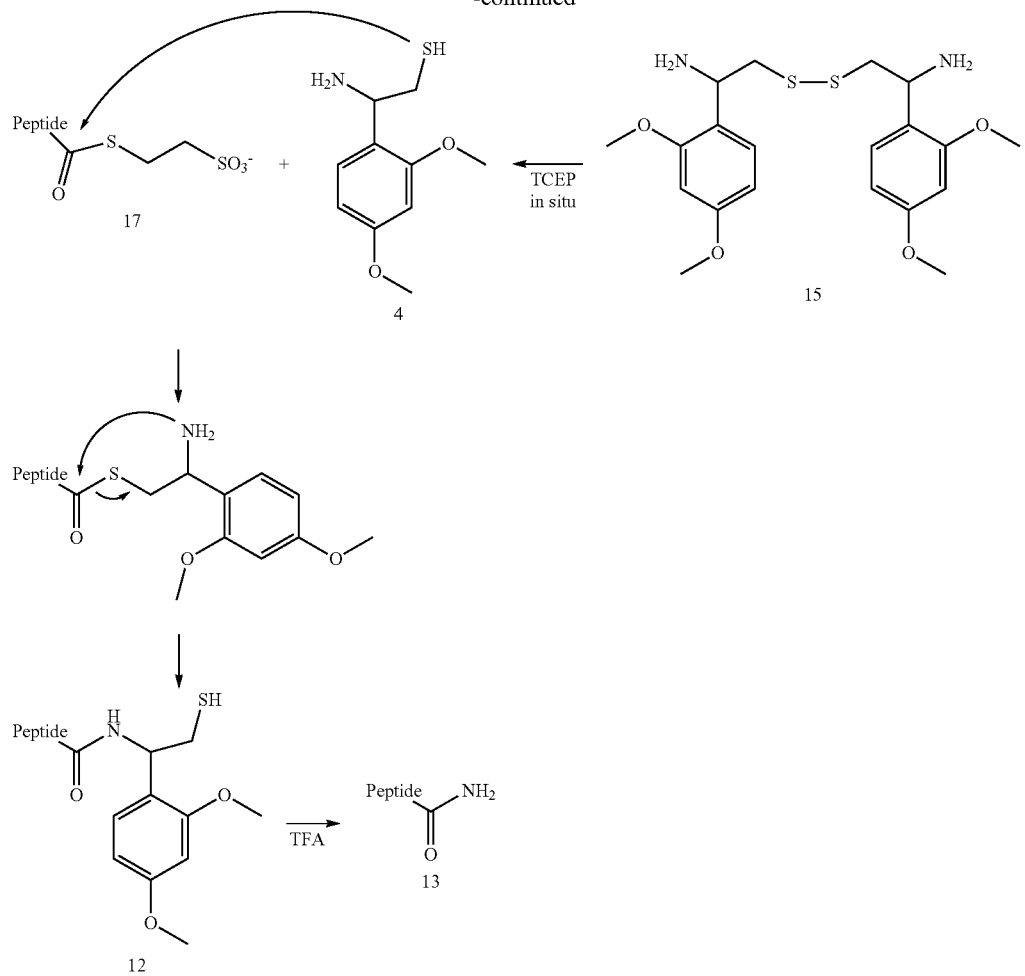

In the example described in Scheme 4, intein was expressed at the C-terminus of Peptide, and a His$_6$ tag was incorporated at the N-terminus for later purification purposes, as well known in the art. The intein moiety generates a peptide thioester in situ upon treatment with a catalyst such as mercapto-ethanesulfonic acid (MESNA) or thiophenol. Scheme 4 outlines the chemical transformations. His-Peptide-intein was first bound to a chitin bead. MESNA was used to trigger the cleavage of N—S shift intermediate, which leads to activated thioester 17.

The chemical mechanism can generally involve two steps. First, there is a coupling or ligation reaction as a result of contacting a C-terminal thioester polypeptide or C-terminal selenoester polypeptide with an auxiliary molecule. Second, there is a treatment to remove a moiety derived from the auxiliary molecule. There are two reactants in the first ligation reaction, the polypeptide to be amidated in its synthetic or recombinant thioester (or selenoester) form and a thiol (or selenol) auxiliary compound with, e.g. a beta or gamma amino or substituted amino group, which can be cleaved off later. First, the thiol (or selenol) in the auxiliary molecule replaces the counterpart in the thioester (or selenoester) in a trans-esterification to form a transient intermediate. This intermediate then undergoes spontaneous intramolecular rearrangement, in which the amino group displaces the thiol (or selenol) to form a stable amide bond. These intermediates are referred to herein as polypeptide adduct having a moiety derived from the auxiliary molecule. Once the polypeptide adduct is formed, a moiety derived from the auxiliary molecule can be removed, e.g., by chemical methods such as acid treatment or irradiation, e.g., ultraviolet irradiation, to produce a C-terminal free amide polypeptide.

With reference to Scheme 4, the activated thioester 17 is contacted with Cmpd 4 which results in formation of Cmpd 12, through a transesterification, and Cmpd 12 stays in solution and thus is easily separable from the intein on chitin bead by filtration. Thus, the thiol in the auxiliary molecule replaces the counterpart in the thioester in a trans-thioesterification reaction to form a transient intermediate. The intermediate then undergoes spontaneous intramolecular rearrangement, in which the amino group displaces the thiol to form a stable amide bond. Cmpd 12 can be treated with an acid, e.g., TFA, to yield Cmpd 13, a C-terminal free amide polypeptide. The His6 tag can be removed afterwards. HPLC traces showed high conversion to 12 and the subsequent four hour trifluoroacetic acid (TFA) treatment gave 70% Cmpd 13.

The reactions contemplated herein can be performed using methods and compounds described herein. Generally, the reaction of the polypeptide which includes a C-terminal thioester or selenoester with the auxiliary molecule (e.g., substituted ethanethiol or ethaneselenol) can be performed in solution. In some embodiments, the auxiliary molecule is in solution and the polypeptide attached to a solid phase support, for example employing methods well known in the art. In one embodiment the auxiliary molecule is a substituted 2-phenyl-2-amino ethanethiol or a substituted 2-phenyl-2-amino ethaneselenol. In one embodiment the solid phase support is an acidic catalyst resin. Such a resin can be used to minimize damage to the polypeptide that may be caused by acid, e.g., TFA, treatment. Since the acid is on a solid support, the acidity is contained in a localized environment, which may remove the auxiliary molecule without adversely affecting the polypeptide. Examples of acidic catalyst resin that may be useful in the invention include fluorosulfonic acid NAFION® SAC-13 polymer (E.I. du Pont de Nemours & Co., Wilmington, Del.) on amorphous silica 10-20% porous nanocomposite) with a pore size of >0.6 ml/g pore volume, >10 nm pore diameter, and >200 m2/g surface area, and a density of 2.1 g/ml at 25° C. This resin is only an example, and persons of ordinary skill with reference to this disclosure will identify other acidic catalyst resins useful in the invention.

The reaction conditions for carrying out the methods of the invention can be various. In one embodiment the methods are carried out at a pH of from 5 to 9. In another embodiment the methods are performed at a pH range of from 6.5 to 8.5. In yet another embodiment the methods are performed at a pH range of 7.0 to 8.0 and in another embodiment at a pH of about 8.0. In one embodiment the ratio of peptide to auxiliary molecule can be from 1:1 to 1:20, but in other embodiments can be from 1:1 to 1:15, or from 1:1 to 1:10, or from 1:1 to 1:5. In a specific embodiment the ratio is 1:1. In different embodiments the reaction time is from about 1 hour to about 24 hours, or from 1 to 15 hours, or from 1 to 12 hours, or from 1 to 8 hours, or from 1 to 6 hours, or from 1 to 4 hours. In one embodiment the temperature of the reaction is room temperature, or about 25° C., but in other embodiments can be about 28° C., or about 27° C., or about 24° C., or about 23° C., or about 20° C., or in a range from 20-27° C., from 22-28° C., or from 23-27° C. In still other embodiments, the temperature of the reaction can be up to 50° C. for the TFA cleavage for the completion of the reaction. In one particular embodiment the reaction time was about 24 hours and the temperature was between 20-27° C. In another embodiment the reaction time is about 48 hours and the temperature is about 50° C. In other embodiments the reaction time is about 6 hours and the temperature about 50° C. But with reference to the disclosure the person of ordinary skill will be able to arrive at other ratios, reaction times, and reaction temperatures suitable to the particular molecules being used that also result in amidation, and these reaction conditions are also contemplated by the disclosure. Each of the above reaction times, reaction temperatures, and ratios are disclosed in all possible combinations as if explicitly set forth herein.

After reaction of the polypeptide having a C-terminal thioester or selenoester with the auxiliary molecule to form the polypeptide adduct having a moiety derived from the auxiliary molecule, the moiety of the auxiliary molecule, or a portion thereof, is removed from the C-terminal of the polypeptide adduct, leaving the amidated polypeptide. For example, in one embodiment the moiety derived from the auxiliary molecule is removed but leaves behind the —NH group that will form the amidation on the C-terminal free amide polypeptide. In one embodiment the polypeptide adduct is a chemical addition product between the polypeptide having the C-terminal thioester or selenoester and the substituted phenyl amino ethanethiol or ethaneselenol auxiliary molecule. In one embodiment the polypeptide adduct is the polypeptide covalently bonded to the substituted phenyl amino ethanethiol or ethaneselenol auxiliary molecule. In one embodiment the polypeptide adduct is formed through the reaction of an amide group on the auxiliary molecule and the —COSR or —COSeR group of the polypeptide. The auxiliary molecule is a molecule, for example, that bears a free SH or SeH group available for reaction with a —COSR or —COSeR group, respectively, to form a new thio or selenoester as an intermediate (i.e., polypeptide adduct), which reacts with the available free amino group to form a polypeptide adduct having an amide bond between the moiety derived from the auxiliary molecule and the polypeptide being amidated.

In some embodiments of methods disclosed herein, the auxiliary molecule is a substituted phenylamino ethanethiol or ethaneselenol molecule. In some embodiments, the auxiliary molecule is a substituted or unsubstituted 2-phenyl-2-amino ethanethiol or a substituted or unsubstituted 2-phenyl-2-amino ethaneselenol. In yet other embodiments the auxiliary molecule is a 2,4-disubstituted phenyl. The 2,4-disubstituted phenyl can be substituted with any of 1, 2, 3, or 4 groups independently selected from any of O—$C_{1-18}$ alkyl, O—$C_{1-8}$ alkyl, O—$C_{1-4}$ alkyl, S—$C_{1-18}$ alkyl, S—$C_{1-8}$ alkyl, S—$C_{1-4}$ alkyl, $C_{1-18}$ alkyl, $C_{1-8}$ alkyl, $C_{1-4}$ alkyl, methoxy, S-alkyl, S-methyl, N-alkyl, N-alkyl$_{1-18}$, N-alkyl$_{1-8}$, N-alkyl$_{1-4}$, N-methyl, and substituted amine. The groups of the substituted phenyl can be any one or any combination of substitutions listed above, which combinations are disclosed as if individually stated herein. In still another embodiment the phenyl is disubstituted with two O-methyl groups at the 2 and 4 positions of the phenyl ring.

In one embodiment the moiety derived from the auxiliary molecule, or a portion thereof, can be removed from the C-terminal of the polypeptide adduct by reaction with an acid. The moiety derived from the auxiliary molecule, or portion thereof, is removed leaving an $NH_2$ group attached at the C-terminal of the polypeptide to complete the amidation of the polypeptide. Trifluoroacetic acid or trifluoromethanesulfonic acid are examples of acids that can be used to remove the auxiliary molecule. In various embodiments from 50% to 100% TFA can be used, and in other embodiments >50% TFA or >60% TFA or >70% TFA or >90% TFA or about 90% TFA or about 95% TFA can be used. In various embodiments any acid with a pKa of 1.0 or lower can be used. In still more embodiments, any weak acid can be used to remove the moiety derived from the auxiliary molecule from the C-terminal of the polypeptide adduct. Weak acids are acids that dissociate incompletely and do not fully release hydrogens in a solution. They do not donate all of their hydrogens. These acids have higher pKa compared to strong acids, which release all of their hydrogens when dissolved in water. Examples of weak acids useful in the invention include, but are not limited to, acetic acid, citric acid, boric acid, phosphoric acid, and hydrofluoric acid.

In other embodiments the moiety derived from the auxiliary molecule is removed from the C-terminal of the C-terminal substituted amide polypeptide by exposure to light, e.g., sun light or ultra-violet rays. Some auxiliary molecules are photocleavable, an example being Cmpd 5.

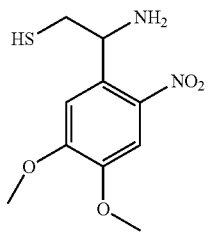

5

Photolysis offers a mild method of cleavage that complements traditional acidic or basic cleavage techniques. With reference to the disclosure the person of ordinary skill will realize effective methods of performing the actual cleavage. In different embodiments the photocleavage can occur at about 365 um over a time period of at least 1 hour. In another embodiment the time period is from 1 hour to 3 hours. References are also available providing reaction conditions and times for performing photocleavage. Holmes et al, *J. Org. Chem.*, 60:2318-19 (1995) and Supplement, pp. 1-7; Dawson et al., *Bioorganic & Medicinal Chemistry* 12 (2004), 2749-57. Also disclosed is a structure of Cmpd 5 where the S is replaced with Se. Methods of using ultra-violet cleavage are known in the art, e.g., U.S. Pat. No. 5,405,783.

In other aspects the auxiliary molecule can be a heterocyclic aryl molecule, some examples including Cmpds 6 and 7 and Formula (VII) following.

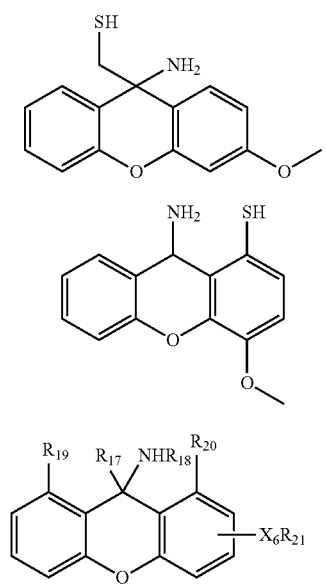

Regarding Formula (VII), $R_{17}$ is H or $X_5H$. $X_5$ is S or Se. $R_{18}$ and $R_{21}$ are independently H, substituted or unsubstituted $C_{1-18}$ alkyl, substituted or unsubstituted $C_{1-8}$ alkyl, substituted or unsubstituted $C_{1-4}$ alkyl or methyl. $X_6$ is O or S. When $R_{17}$ is H, then either $R_{19}$ or $R_{20}$ is $X_5H$ and the other is H. In some embodiments, $R_{18}$ is H. In some embodiments, $R_{18}$ is methyl.

These auxiliary molecules can also be contacted with a respective polypeptide thioester or selenoester compound to produce amidation on the polypeptide, for example an amidation at the C-terminal of the polypeptide. The reaction conditions and techniques disclosed herein with respect to Formula (I) and other auxiliary molecules also apply to the heteroaryl auxiliary molecules and other auxiliary molecules disclosed herein. In one embodiment these heteroaryl auxiliary molecules can be cleaved to form the amide under milder conditions than above, such as 1% TFA treatment, or 2% or 3% or 4% or 5% TFA treatment.

There are also provided novel molecules such as the 2-amino-2-(2,4-dimethoxyphenyl)ethanethiol (4) and 2-amino-2-(2,4-dimethoxyphenyl)ethaneselenol auxiliary molecules, as depicted in Formula (V). These auxiliary molecules can also be present in a dimerized form (Formula (VI), or Cmpd 15 for the 2-amino-2-(2,4-dimethoxyphenyl) ethanethiol dimer, where X is S or Se). The dimerized form is produced by an iodination reaction of 14 as described in Scheme 7 below. Procedures to prepare 14 were previously reported by Macmillan and Anderson, *Organic Letters*, 6(25): 4659-62 (2004).

With reference to Scheme 7, in these reactions a methanol solution containing 14 was treated with $I_2$ solution in acetic acid. After 10 minutes, saturated aqueous sodium thiosulfate was added to quench the excess iodine and the crude was purified by reverse phase HPLC to give the dimer 15. The dimer can be used as a starting material and can be converted to monomers in situ by TCEP (tris(2-carboxyethyl)phosphine) or thiophenol to the monomer 4. The dimer provides improved stability over the monomer and is easily synthesized and purified. The monomer will, however, air oxidize into the dimer during storage. Trt in 14 refers to a trityl group.

Additional variations on the methods and molecules are possible and contemplated by the disclosure. In one embodiment of the invention a more labile auxiliary can be used. For example, the Sieber based Cmpd 6 or a photocleavable auxiliary, such as Cmpd 5, can be used. Cmpd 6 as an auxiliary can be readily removed with about 1% TFA or, in various other embodiments, about 2% or about 3% or about 4% or about 5% TFA. Cmpd 5 as an auxiliary molecule can be removed by ultra-violet radiation. The use of such an auxiliary carries the advantages of less damage to the protein/peptide product, as well as improvements in process and yield.

EXAMPLES

The following examples are to further illustrate the description herein and are not intended to limit the scope of the claims.

Example 1

Production of Peptides and Thioesters

Peptides were synthesized on ABI 433A synthesizers with either Boc or Fmoc chemistry. Preparative reverse-phase HPLC was performed on a Waters HPLC/MS system consisting of Waters 2525 Prep HPLC Pump, 2767 sample manager, 2487 dual absorbance detector and Micromass ZQ mass spectrometer. The crude peptide was purified using Waters preparative HPLC/MS instrument with Kromasil C4 columns using a linear gradient (25-45%) of buffer B in buffer A over 30 min (buffer A=0.05% TFA in water; buffer B=0.05% TFA in AcCN) and a flow rate of 20 mL/min. Analytical reverse-phase HPLC was performed on an Agilent 1100 system equipped with a 6120 quadrupole LC/MS.

Thioester was prepared on a 433A peptide synthesizer employing t-Butylcarbonyl (t-Boc) chemistry with in situ neutralization protocol. Standard Boc amino acids and suitable pre-loaded amino acid-SCH$_2$CO-Leu-OCH$_2$-Pam resin with loadings of about 0.55 mmol/g were used. The peptide thioester was cleaved using standard HF cleavage condition with p-cresol as scavenger. Formyl and DNP groups remained on the peptide and were removed during or after the ligation reaction. The crude peptide was purified using Waters preparative HPLC/MS instrument with a Kromasil 250×21.2 mm C4 column using a linear gradient (25-45%) of buffer B in buffer A over 30 min (buffer A=0.05% TFA in water; buffer B=0.05% TFA in ACN) and a flow rate of 20 mL/min. The fractions were analyzed by the Agilent analytical HPLC/MS and the pure fractions were pooled and lyophilized. A typical 0.2 mmol scale synthesis yielded 65.0 mg peptide thioester.

Example 2

Amidation of GIP Analog Peptide

With reference to Scheme 2 following, a mixture of a thioester of a GIP analog (i.e., GIP(1-30)-GlyGly-COSR, R=—CH$_2$CO-Leu-OH, 5.5 mg) and 15 (i.e., 4 in dimerized form) (1.0 mg, ca. 2.5 equiv., in a TFA salt form) were dissolved in 1 mL 6M guanidine, pH 7.5 with 200 mM sodium phosphate and 20 mM TCEP. Thiophenol (0.1 v/v %) was added and the reaction was monitored by HPLC at 1 hour, which showed complete conversion to peptide 104b with molecular weight addition of 8 Dalton from the thioester. The crude was purified by preparative HPLC with a Kromasil 250×10 mm C4 column using a linear gradient (25-45%) of buffer B in buffer A over 30 min (buffer A=0.05% TFA in water; buffer B=0.05% TFA in ACN) and a flow rate of 5 mL/min to give 1.6 mg of 104b. Purified 104b was treated with TFA mixture (95% TFA+5% triiso-propylsilane (TIS) for 4 hours and analyzed with LCMS, which showed one major peak, the molecular weight of which corresponding to that of Cmpd 3 (molecular weight decrease of 196.5 Dalton from 104b). The amino acid sequence of GIP(1-30) is known in the art, e.g., US Publication No. 2008/0312157, the disclosure of which is incorporated by reference herein in its entirety. In Scheme 2, the term "GIP" refers to GIP(1-30)-GG, YAEGTFISDYSIAMDKIHQQDFVNWLLAQKGG (SEQ ID NO:25).

Scheme 2

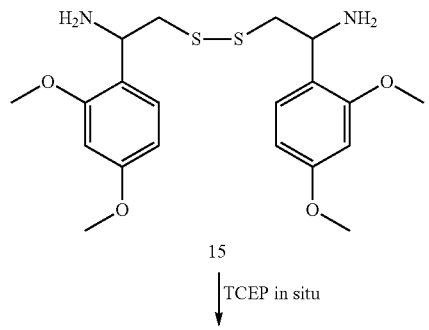

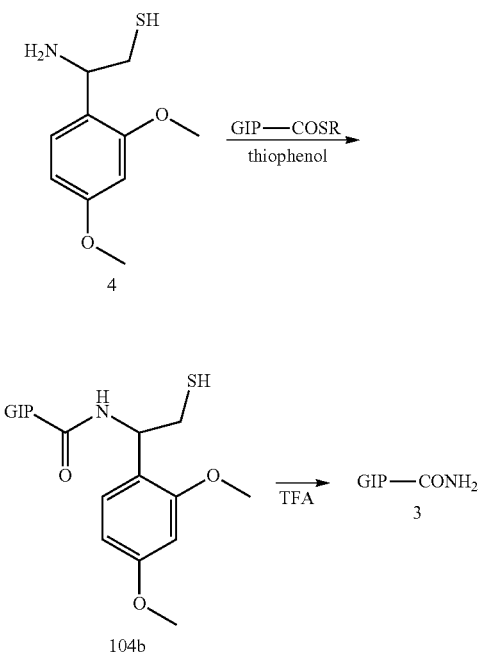

Example 3

Amidation of Exendin-4 Analog Peptide

With reference to Scheme 3 following, a mixture of a thioester of an exendin analog (i.e., exendin-4(1-28)-miniPEG3-Lys-COSR, R=—CH$_2$CO-Leu-OH, 5.2 mg) and dimerized 15 (1.0 mg, ca. 2.5 equiv., in a TFA salt form) were dissolved in 1 mL 6 M guanidine, pH 7.5 with 200 mM sodium phosphate and 20 mM TCEP. Thiophenol (0.1 v/v %) was added and the reaction was monitored by HPLC at 1 hour, which showed complete conversion to peptide 104a (molecular weight addition of 8 Dalton, not counting the loss of a DNP protection group on Histidine in the thioester during this reaction). The crude was purified by preparative HPLC with a Kromasil 250×10 mm C4 column using a linear gradient (25-45%) of buffer B in buffer A over 30 min (buffer A=0.05% TFA in water; buffer B=0.05% TFA in ACN) and a flow rate of 5 mL/min to give 2.1 mg of 104a. Purified 104a was treated with TFA mixture (95% TFA+5% TIS (tri-isopropyl silane)) for 4 hours and analyzed with LCMS, which showed 55% conversion to a product, the molecular weight of which corresponding to that of 5 (molecular weight decrease of 196.5 Dalton from 104a). The amino acid sequence of exendin-4(1-28) is known in the art, e.g., U.S. Pat. No. 7,452,858, the disclosure of which is incorporated by reference herein in its entirety. In Scheme 3, the term "Ex" refers to exendin-4(1-28), HGEGTFTSDLSKQMEEEAVR-LFIEWLKN (SEQ ID NO:26).

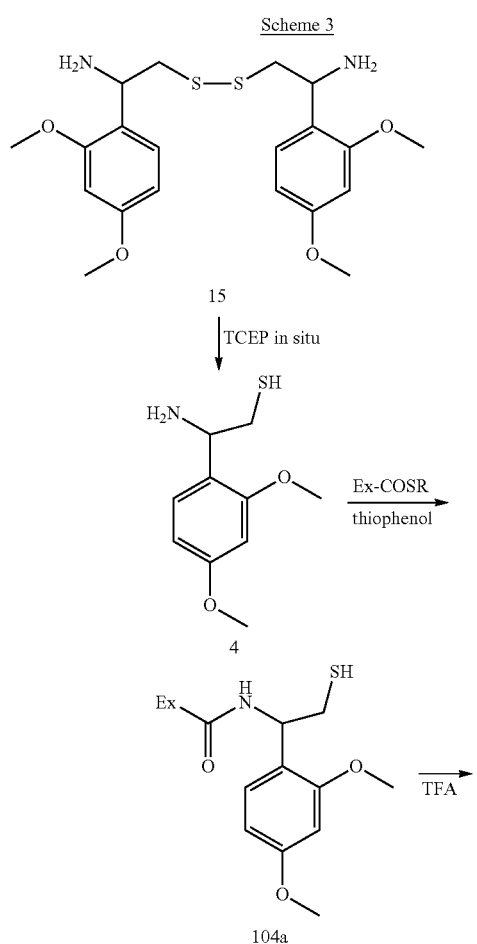

Scheme 3

Example 4

Amidation of a Recombinant Peptide

Construction of a Peptide-Intein Fusion Protein:

For purposes of this example, "Peptide" has the amino acid sequence HGEGTFTSDLSKQLEEEAVRLFIEWLKQGGP SKEIISGGGKCNTATCVLGRLSQELHR- LQTYPRTNTGSNTY (SEQ ID NO:27). The DNA sequence of "Peptide" was obtained by back translation of the amino acid sequence using codons optimal for bacterial expression, using method well known in the art. The gene was constructed by using the overlapping oligonucleotides extension PCR. The PCR products were gel purified and digested with restriction enzymes Nde I and Spe I, as well as the plasmid pTXB1 (New England Biolab). The digestion reaction products were gel purified and ligated together to give pTXB190, in which the "Peptide" gene was located at the N-terminus and in frame with the intein gene. The final expression construct was confirmed by DNA sequencing analysis using T7 forward primer.

Expression and Purification of "Peptide"-Intein Fusion Protein

The expression of plasmid pTXB190 was conducted in BL21(DE3) cells at 30° C. overnight. The cells were pelleted by centrifugation at 5,000×g for 15 minutes and the cell pellets were re-suspended in 100 ml lysis buffer (50 mM Tris, pH 8.0, 150 mM NaCl) plus protease inhibitors for each liter of culture. The re-suspended cell solution was passed twice through a microfluidizer at 100 PSI (min). The chamber was (and should be) kept in ice water throughout the entire process. The fluidized slurry was centrifuged at 14000×g for 30 min. The supernatant was then removed and retained on ice.

A chitin bead (New England Bio Lab, Ipswich, Mass.) column was packed using 1 ml of the bead for every 2 mg of "Peptide"-intein fusion protein in the cell lysate, and washed with 5 column volumes of lysis buffer. Thus, the cell lysate supernatant was added to the chitin column and the fall through was collected. After the sample finished loading, the column was washed with lysis buffer until no protein eluted, as determined by protein assay. The beads were washed with 2-3 column volumes of 50 mM phosphate buffer, pH 7.4 before the amidation reaction.

Amidation Procedure of "Peptide"

With reference to Scheme 4, "Peptide"-intein attached to chitin beads (ca. 2 mg/mL) and the dimerized 15 auxiliary molecule (5 equiv., in a TFA salt form) were combined in the presence of 0.1 M Tris, pH 8.0, 10 mM TCEP and 10 mM 2-mercaptoethanesulfonic acid (MESNA). The solution was slightly shaken for overnight at room temperature. The beads were filtered and the aqueous phase dialyzed, lyophilized and analyzed by HPLC to show that the major peak was the desired product 12. The crude 12 was treated with 90% TFA/ 5% TIS/5% H$_2$O for 4 hours. Crude HPLC showed about 70% conversion to final product 13 or "Peptide."

Example 5

Preparation of Dimer Cmpd 15

With reference to Scheme 7 following, Cmpd 14 was synthesized following literature procedures (Macmillan D. et al. *Org. Lett.*, 2004, 6, 4659-4662).

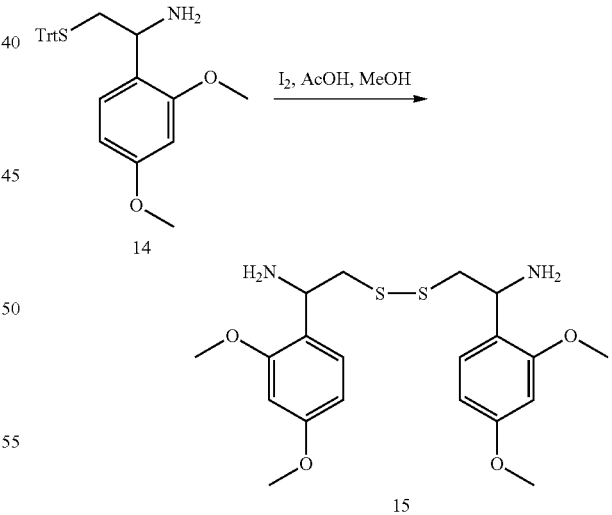

Scheme 7

Cmpd 14 was dissolved in minimum amount of MeOH and 1.2 equiv. of 0.125 M I$_2$ in AcOH was added dropwise and the reaction mixture was stirred for 30 min before Na$_2$S$_2$SO$_3$ was added to quench the I$_2$. The crude was diluted with water and purified by HPLC to give 15 in TFA salt form and as a mixture of diastereomers (the two diastereomer peaks from HPLC were pooled, 49.5%). $^1$H-NMR (300 MHz, CD$_3$OD): δ=7.18 (2H, m, DMB), 6.61 (2H, m, DMB), 6.56 (2H, m, DMB), 4.63

(2H, m, benzylic CH), 3.88 (3H, s, OMe), 3.82 (3H, s, OMe), 3.81 (3H, s, OMe), 3.79 (3H, s, OMe), 3.25 (3H, m, CH$_2$), 3.12 (1H, m, CH$_2$). $^{13}$C-NMR (75 MHz, CD$_3$OD): δ=164.00, 160.04, 131.34, 131.00, 116.19 (CF$_3$ in TFA), 106.54, 106.49, 100.25, 100.16, 56.33, 56.17, 52.28, 51.46, 40.91, 40.74. m/z (ESI): 425.21 [MH]+, C$_{20}$H$_{28}$N$_2$O$_4$S$_2$ calcd. M 424.15.

Example 6

Synthesis of Heteroaryl Auxiliary Cmpd 6

With reference to Scheme 8 following, 3-methoxy xanthen-9-one 201 is converted to 9-methylene-9H-xanthene 202 with Grignard reagent MeMgCl. See De la Fuente, et al., *Journal of Organic Chemistry*, 2006, 71:3963-3966. Cmpd 202 is converted to 203 by Sharpless' regioselective aminohydroxylation. See Reddy, K. L. & Sharpless, K. B. *J. Am. Chem. Soc.*, 1998, 120:1207. The thioacetic acid is then introduced by Mitsunobo reaction to form 204. See Rozwadowska, M. D. *Tetrahedron* 1997, 53:10615. Subsequent deprotection reactions by sodium methoxide and then TFA afford Cmpd 6.

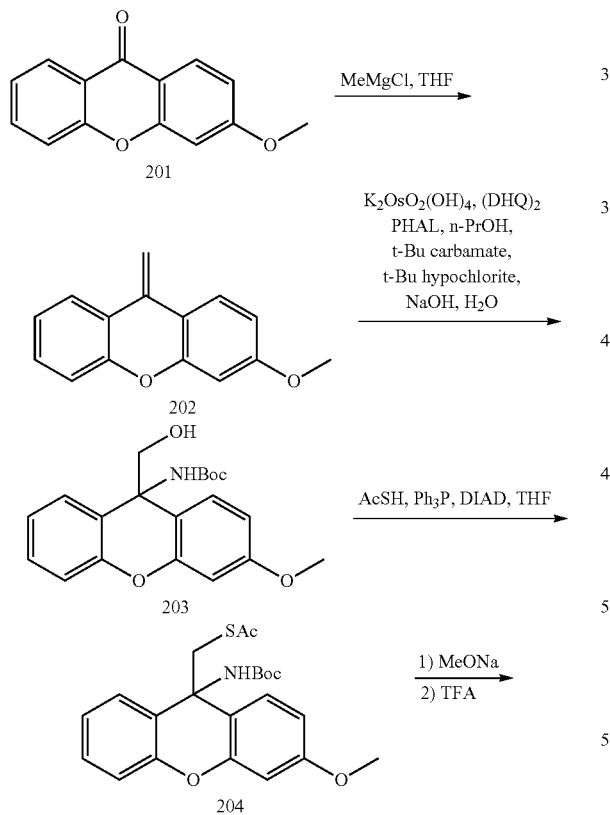

Example 7

Preparation of Heteroaryl Auxiliary Molecule Cmpd 7

With reference to Scheme 5 following, 4-methoxy xanthen-9-one is brominated to give 1-bromo-4-methoxy xanthen-9-one. See e.g., de la Fuente, M. & Dominguez, D., *Tetrahedron* 60 (2004) 10019-10028. The ketone is converted to amine in a two step procedure with NaBH$_4$ and ammonium bicarbonate. The bromide is then converted to thiol by treatment of sodium sulfide to provide Cmpd 7.

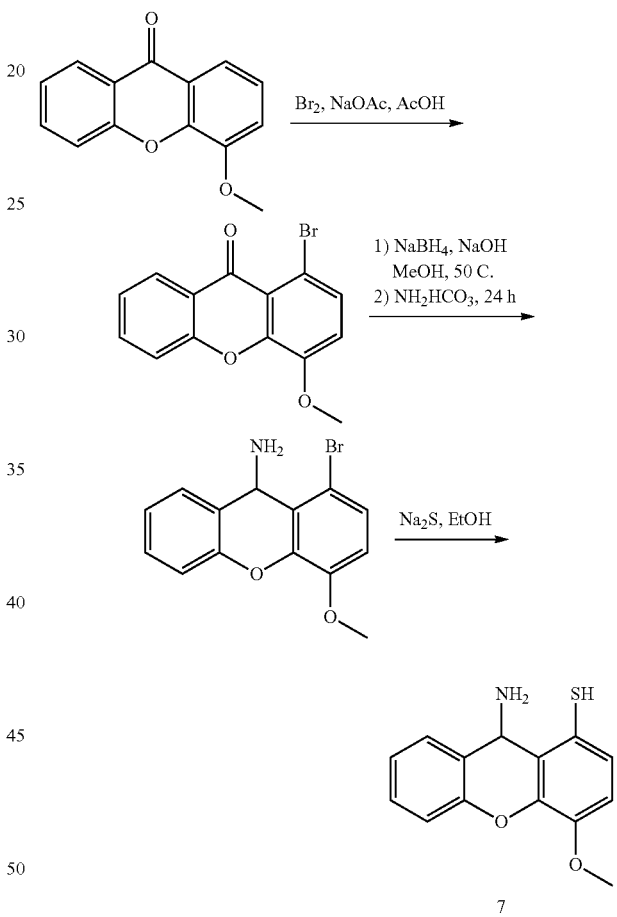

Example 8

Preparation of Dimer 16

With reference to Scheme 6 following, the commercially available 2-bromo-1-(4,5-dimethoxy-2-nitrophenyl)ethanone is treated with trityl thiol to give the desired thioether product. The ketone is converted to a primary amine by reductive amination with sodium cyanoborohydride and ammonium acetate. Following iodine treatment the desired dimerized product 16 is generated.

Scheme 6

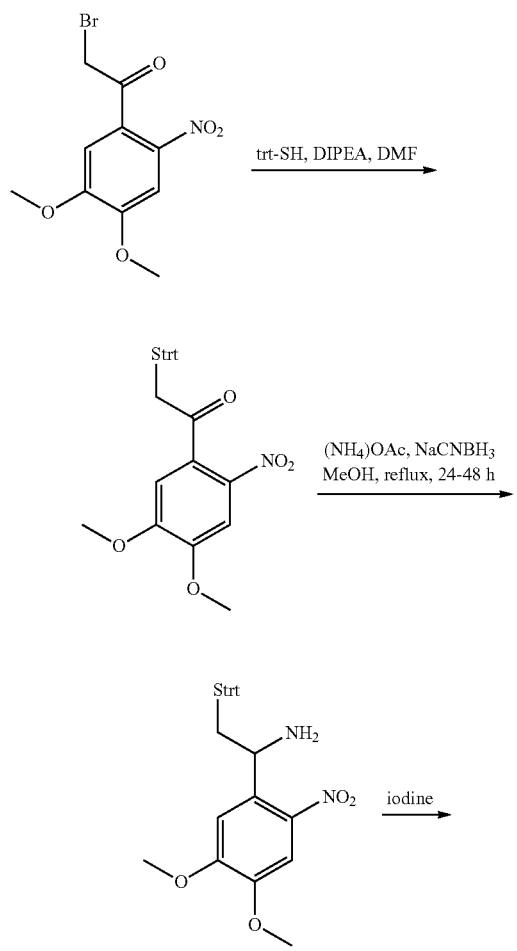

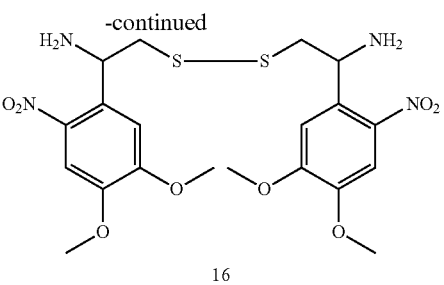

16

Example 9

Preparation of Auxiliary Molecule 5

With reference to Scheme 9 following, and as an alternative method, Cmpd 205 is prepared using available methods. See e.g., Chiara Marinzi, et al., *Bioorganic & Medicinal Chemistry*, 2004, 12:2749-2757. The compound is then treated with sodium methoxide followed by TFA to remove the protecting groups and to afford Cmpd 5.

Scheme 9

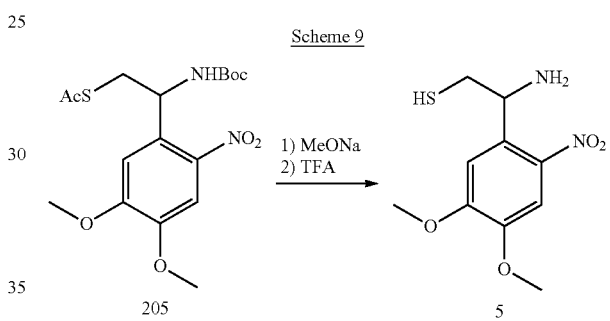

V. Informal sequence listing

```
                                             (SEQ ID NO: 1)
Rat amylin: KCNTATCATQRLANFLVRSSNNLGPVLPPTNVGSNTY.

(SEQ ID NO: 2)
Human amylin: KCNTATCATQRLANFLVHSSNNFGAILSSTNVGSNTY.

(SEQ ID NO: 3)
Pramlintide: KCNTATCATQRLANFLVHSSNNFGPILPPTNVGSNTY.

(SEQ ID NO: 4)
Human calcitonin: CGNLSTCMLGTYTQDFNKFHTFPQTAIGVGAP.

(SEQ ID NO: 5)
Salmon calcitonin: CSNLSTCVLGKLSQELHKLQTYPRTNTGSGTP.

(SEQ ID NO: 6)
Davalintide: KCNTATCVLGRLSQELHRLQTYPRTNTGSNTY.

(SEQ ID NO: 7)
Exendin-3: HSDGTFTSDLSKQMEEEAVRLFIEWLKNGGPSSGAPPPS-NH₂.

(SEQ ID NO: 8)
Exendin-4: HGEGTFTSDLSKQMEEEAVRLFIEWLKNGGPSSGAPPPS-NH₂.

(SEQ ID NO: 9)
GLP-1[7-36]: HAEGTFTSDVSSYLEGQAAKEFIAWLVKGRG.
```

-continued

Metreleptin:
(SEQ ID NO: 10)
MVPIQKVQDDTKTLIKTIVTRINDISHTQSVSSKQKVTGLDFIPGLHPILTLSKMD
QTLAVYQQILTSMPSRNVIQISNDLENLRDLLHVLAFSKSCHLPWASGLETLDSLGGVLE
ASGYSTEVVALSRLQGSLQDMLWQLDLSPGC (SEQ ID NO: 11)
Human PP: APLEPVYPGDNATPEQMAQYAADLRRYINMLTRPRY-NH₂.

(SEQ ID NO: 12)
PYY: YPIKPEAPGEDASPEELNRYYASLRHYLNLVTRQRY-NH2.

(SEQ ID NO: 13)
NPY: YPSKPDNPGEDAPAEDMARYYSALRHYINLITRQRY-NH₂.

(SEQ ID NO: 14)
Human GIP: YAEGTFISDYSIAMDKIHQQDFVNWLLAQKGKKNDWKHNITQ.

Human insulin translation product:
(SEQ ID NO: 15)
MALWMRLLPLLALLALWGPDPAAAFVNQHLCGSHLVEALYLVCGERGFFYTPKTRRE
AEDLQVGQVELGGGPGAGSLQPLALEGSLQKRGIVEQCCTSICSLYQLENYCN.

Human growth hormone translation produce:
(SEQ ID NO: 16)
MATGSRTSLLLAFGLLCLPWLQEGSAFPTIPLSRLFDNAMLRAHRLHQLAFDTYQEFEE
AYIPKEQKYSFLQNPQTSLCFSESIPTPSNREETQQKSNLELLRISLLLIQSWLEPVQFLRS
VFANSLVYGASDSNVYDLLKDLEEGIQTLMGRLEDGSPRTGQIFKQTYSKFDTNSHNDD
ALLKNYGLLYCFRKDMDKVETFLRIVQCRSVEGSCGF.

Synthetic human erthyropoietin construct:
(SEQ ID NO: 17)
MATGSRTSLLLAFGLLCLPWLQEGSAFPTIPLSRLFDNAMLRAHRLHQLAFDTYQEFEE
AYIPKEQKYSFLQNPQTSLCFSESIPTPSNREETQQKSNLELLRISLLLIQSWLEPVQFLRS
VFANSLVYGASDSNVYDLLKDLEEGIQTLMGRLEDGSPRTGQIFKQTYSKFDTNSHNDD
ALLKNYGLLYCFRKDMDKVETFLRIVQCRSVEGSCGF.

Human cholecystokinin (CCK) prohormone:
(SEQ ID NO: 18)
MNSGVCLCVLMAVLAAGALTQPVPPADPAGSGLQRAEEEAPRRQLRVSQRTDGESRAHL
GALLARYIQQARKAPSGRMSIVKNLQNLDPSHRISDRDYMGWMDFGRRSAEEYEYPS.

Glucagon-like peptide-2 (GLP-2):
(SEQ ID NO: 19)
HADGSFSDEMNTILDNLAARDFINWLIQTKITDR.

Neurotensin:
(SEQ ID NO: 20)
MMAGMKIQLVCMLLLAFSSWSLCSDSEEEMKALEADFLTNMHTSKISKAHVPSWKMT
LLNVCSLVNNLNSPAEETGEVHEEELVARRKLPTALDGFSLEAMLTIYQLHKICHSRAFQ
HWELIQEDILDTGNDKNGKEEVIKRKIPYILKRQLYENKPRRPYILKRDSYYY.

Urocortin:
(SEQ ID NO: 21)
MRQAGRAALLAALLLLVQLCPGS SQRSPEAAGVQDPSLRWSPGARNQGGGARALLLLL
AERFPRRAGPGRLGLGTAGERPRRDNPSLSIDLTFHLLRTLLELARTQSQRERAEQNRIIF
DSVGK.

Neuromedin U:
(SEQ ID NO: 22)
MLRTESCRPRSPAGQVAAASPLLLLLLLLAWCAGACRGAPILPQGLQPEQQLQLWNEID
DTCSSFLSIDSQPQASNALEELCFMIMGMLPKPQEQDEKDNTKRFLFHYSKTQKLGKSN
VVSSVVHPLLQLVPHLHERRMKRFRVDEEFQSPFASQSRGYFLFRPRNGRRSAGFI.

Neuromedin S precursor:
(SEQ ID NO: 23)
MKHLRPQFPLILAIYCFCMLQIPSSGFPQPLADPSDGLDIVQLEQLAYCLSQWAPLSRQPK
DNQDIYKRFLFHYSRTQEATHPVKTGFPPVHPLMHLAAKLANRRMKRILQRGSGTAAV
DFTKKDHTATWGRPFFLFRPRNGRNIEDEAQIQW.

-continued

Neuromedin B:
(SEQ ID NO: 24)
MARRAGGARMFGSLLLFALLAAGVAPLSWDLPEPRSRASKIRVHSRGNLWATGHFMG
KKSLEPSSPSHWGQLPTPPLRDQRLQLSHDLLGILLLKKALGVSLSRPAPQIQYRRLLVQI
LQK.

(SEQ ID NO: 25)
GIP(1-30-GG: YAEGTFISDYSIAMDKIHQQDFVNWLLAQKGG.

(SEQ ID NO: 26)
Exendin-4(1-28): HGEGTFTSDLSKQMEEEAVRLFIEWLKN.

Fusion Peptide of Example 4

15

(SEQ ID NO: 27)
HGEGTFTSDLSKQLEEEAVRLFIEWLKQGGPSKEIISGGGKCNTATC

VLGRLSQELHRLQTYPRTNTGSNTY.

---

What is claimed is:

1. A method for producing a C-terminal free amide polypeptide, the method comprising:
  contacting a C-terminal thioester polypeptide with a moiety, wherein said moiety has the structure of Cmpd 4 or Cmpd 5:

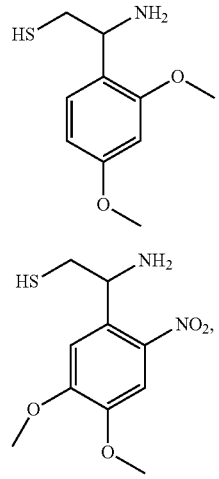

thereby forming a C-terminal substituted amide polypeptide substituted with the moiety; and
  removing a portion of the moiety and leaving the amide nitrogen to produce the amidated polypeptide, thereby forming said C-terminal free amide polypeptide.

2. A method for producing a C-terminal free amide polypeptide, comprising:
  1) contacting a C-terminal thioester or selenoester polypeptide with a moiety, wherein said moiety is:
    (a) a substituted or unsubstituted 2-phenyl-2-amino ethanethiol or 2-phenyl-2-amino ethaneselenol, thereby forming a C-terminal substituted amide polypeptide substituted with the 2-phenyl-2-amino ethanethiol or 2-phenyl-2-amino ethaneselenol, wherein said substituted or unsubstituted 2-phenyl-2-amino ethanethiol and said substituted or unsubstituted 2-phenyl-2-amino ethaneselenol have the structure of Formula (I):

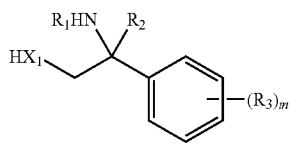

wherein
  $X_1$ is S or Se;
  $R_1$ is H;
  $R_2$ is H, cyano, halo, substituted or unsubstituted $C_{1-18}$ alkyl, substituted or unsubstituted $C_{1-18}$ alkoxy, substituted or unsubstituted $C_{5-14}$ aryl, or substituted or unsubstituted $C_{5-14}$ heteroaryl;
  $R_3$ at each occurrence is independently H, substituted or unsubstituted $C_{1-18}$ alkyl, substituted or unsubstituted $C_{5-14}$ aryl, substituted or unsubstituted $C_{5-14}$ heteroaryl, substituted or unsubstituted $C_{1-18}$ alkoxy, cyano, nitro or halo;
  and
  m is 0 to 5; or (b) a compound having the structure of Formula (III):

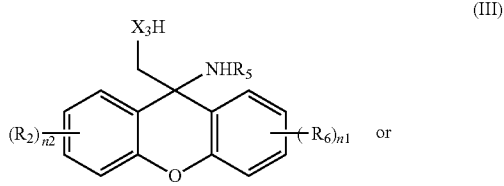

-continued

Formula (IV):

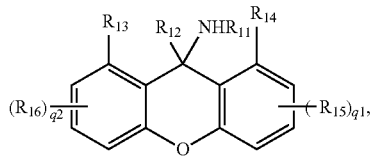

thereby forming a C-terminal substituted amide polypeptide substituted with the compound of Formula (III) or (IV), wherein $X_3$ is S or Se;

$R_5$ is H;

$R_6$ and $R_7$ are each independently H, cyano, nitro, halo, substituted or unsubstituted $C_{1-18}$ alkyl, substituted or unsubstituted $C_{1-18}$ alkoxy, substituted or unsubstituted $C_{5-14}$ aryl, or substituted or unsubstituted $C_{5-14}$ heteroaryl;

n1 and n2 are independently 0-4; wherein when said C-terminal thioester polypeptide is contacted, then $X_3$ is S, and when said C-terminal selenoester is contacted, then $X_3$ is Se;

$R_{11}$ is H;

$R_{12}$ is H, cyano, halo, substituted or unsubstituted $C_{1-18}$ alkyl, substituted or unsubstituted $C_{1-18}$ alkoxy, substituted or unsubstituted $C_{5-14}$ aryl or substituted or unsubstituted $C_{5-14}$ heteroaryl;

one of $R_{13}$ or $R_{14}$ is S or Se, and the other is H, cyano, nitro, halo, substituted or unsubstituted $C_{1-18}$ alkyl, substituted or unsubstituted $C_{1-18}$ alkoxy, substituted or unsubstituted $C_{5-14}$ aryl or substituted or unsubstituted $C_{5-14}$ heteroaryl;

$R_{15}$ and $R_{16}$ are independently H, cyano, nitro, halo, substituted or unsubstituted $C_{1-18}$ alkyl, substituted or unsubstituted $C_{1-18}$ alkoxy, substituted or unsubstituted $C_{5-14}$ aryl or substituted or unsubstituted $C_{5-14}$ heteroaryl; and q1 and q2 are independently 0 to 3;

wherein when said C-terminal thioester polypeptide is contacted, then $R_{13}$ or $R_{14}$ is S; and when said C-terminal selenoester polypeptide is contacted, then $R_{13}$ or $R_{14}$ is Se; and 2) removing a portion of the moiety and leaving the amide nitrogen to produce the amidated polypeptide, thereby forming said C-terminal free amide polypeptide;

wherein said C-terminal thioester polypeptide or said C-terminal selenoester polypeptide is attached to a solid support.

3. A method for producing a C-terminal free amide polypeptide, comprising:

1) contacting a C-terminal thioester or selenoester polypeptide with a moiety, wherein said moiety is:

(a) a substituted or unsubstituted 2-phenyl-2-amino ethanethiol or 2-phenyl-2-amino ethaneselenol, thereby forming a C-terminal substituted amide polypeptide substituted with the 2-phenyl-2-amino ethanethiol or 2-phenyl-2-amino ethaneselenol, wherein said substituted or unsubstituted 2-phenyl-2-amino ethanethiol and said substituted or unsubstituted 2-phenyl-2-amino ethaneselenol have the structure of Formula (I):

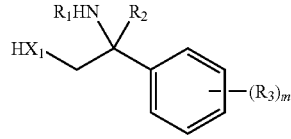

wherein $X_1$ is S or Se;

$R_1$ is H;

$R_2$ is H, cyano, halo, substituted or unsubstituted $C_{1-18}$ alkyl, substituted or unsubstituted $C_{1-18}$ alkoxy, substituted or unsubstituted $C_{5-14}$ aryl, or substituted or unsubstituted $C_{5-14}$ heteroaryl;

$R_3$ at each occurrence is independently H, substituted or unsubstituted $C_{1-18}$ alkyl, substituted or unsubstituted $C_{5-14}$ aryl, substituted or unsubstituted $C_{5-14}$ heteroaryl, substituted or unsubstituted $C_{1-18}$ alkoxy, cyano, nitro or halo;

and m is 0 to 5; or b) a compound having the structure of

Formula (III):

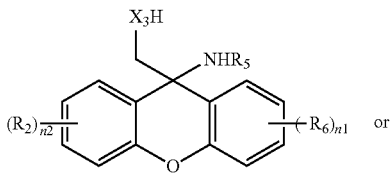

Formula (IV):

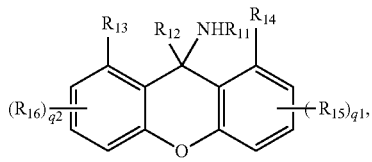

thereby forming a C-terminal substituted amide polypeptide substituted with the compound having the structure of Formula (III) or (IV), wherein $X_3$ is S or Se;

$R_5$ is H;

$R_6$ and $R_7$ are each independently H, cyano, nitro, halo, substituted or unsubstituted $C_{1-18}$ alkyl, substituted or unsubstituted $C_{1-18}$ alkoxy, substituted or unsubstituted $C_{5-14}$ aryl, or substituted or unsubstituted $C_{5-14}$ heteroaryl;

n1 and n2 are independently 0-4; wherein when said C-terminal thioester polypeptide is contacted, then $X_3$ is S, and when said C-terminal selenoester is contacted, then $X_3$ is Se;

$R_{11}$ is H;

$R_{12}$ is H, cyano, halo, substituted or unsubstituted $C_{1-18}$ alkyl, substituted or unsubstituted $C_{1-18}$ alkoxy, substituted or unsubstituted $C_{5-14}$ aryl or substituted or unsubstituted $C_{5-14}$ heteroaryl;

one of $R_{13}$ or $R_{14}$ is S or Se, and the other is H, cyano, nitro, halo, substituted or unsubstituted $C_{1-18}$ alkyl, substituted or unsubstituted $C_{1-18}$ alkoxy, substituted or unsubstituted $C_{5-14}$ aryl or substituted or unsubstituted $C_{5-14}$ heteroaryl;

$R_{15}$ and $R_{16}$ are independently H, cyano, nitro, halo, substituted or unsubstituted $C_{1-18}$ alkyl, substituted or unsubstituted $C_{1-18}$ alkoxy, substituted or unsubstituted $C_{5-14}$ aryl or substituted or unsubstituted $C_{5-14}$ heteroaryl; and q1 and q2 are independently 0 to 3;

wherein when said C-terminal thioester polypeptide is contacted, then $R_{13}$ or $R_{14}$ is S; and when said C-terminal selenoester polypeptide is contacted, then $R_{13}$ or $R_{14}$ is Se; and 2) removing a portion of the moiety and leaving the amide nitrogen to produce the amidated polypeptide, thereby forming said C-terminal free amide polypeptide;

wherein said portion of the moiety is removed by reaction with an acid; and wherein said acid is a solid support acidic catalyst resin.

4. The method of claim 1, wherein said C-terminal thioester polypeptide comprises a polypeptide moiety selected from the group consisting of pramlintide moiety, exendin-4 moiety, davalintide moiety, glucagon-like peptide-1(7-7) [GLP-1(7-37)] moiety, meterleptin moiety, peptide-YY (3-36) [PYY(3-36)] moiety, gastric inhibitory polypeptide (GIP) moiety, insulin moiety, human growth hormone (HGH) moiety, erythropoietin (EPO) moiety, cholecystokinin (CCK) moiety, glucagon-like peptide-1 (GLP-2) moiety, GLP-1/glucagon chimeric peptide moiety, CLP-1/GIP chimeric peptide moiety, neurotensin moiety, urocortin moiety, neuromedin moiety, and hybrid thereof.

5. The method of claim 1, whereat said C-terminal thioester polypeptide is attached to a solid support.

6. The method of claim 1, wherein said portion of the moiety is removed by reaction with acid.

7. The method of claim 6, wherein said acid is tri-fluoroacetic acid or trifluoromethanesulfonic acid.

8. The method of claim 6, wherein said acid is a solid support acidic catalyst resin.

9. The method of claim 4, wherein said polypeptide moiety is the exendin-4 moiety.

10. The method of claim 2, wherein said moiety has the structure of Cmpd 4 or Cmpd 5:

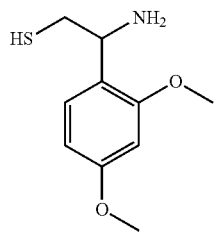

4

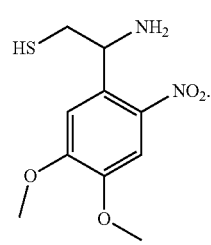

5

11. The method of claim 2, wherein said portion of the moiety is removed by reaction with an acid.

12. The method of claim 11, wherein said acid is tri-fluoroacetic acid or trifluoromethanesulfonic acid.

13. The method of claim 11, wherein said acid is a solid support acidic catalyst resin.

14. The method of claim 2, wherein said C-terminal thioester or selenoester polypeptide comprises a polypeptide moiety selected from the group consisting of pramlintide moiety, exendin-4 moiety, davalintide moiety, glucagon-like peptide-1(7-37) [GLP-1(7-37)]moiety, meterleptin moiety, peptide-YY (3-36) [PYY(3-36)] moiety, gastric inhibitory polypeptide (GIP) moiety, insulin moiety, human growth hormone (HGH) moiety, erythropoietin (EPO) moiety, cholecystokinin (CCK) moiety, glucagon-like peptide-1 (GLP-2) moiety, GLP-1/glucagon chimeric peptide moiety, GLP-1/GIP chimeric peptide moiety, neurotensin moiety, urocortin moiety, neuromedin moiety, and hybrid thereof.

15. The method of claim 14, wherein said polypeptide moiety is the exendin-4 moiety.

16. The method of claim 3, wherein said moiety has the structure of Cmpd 4 or Cmpd 5:

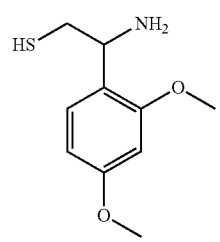

4

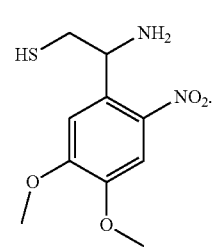

5

17. The method of claim 3, wherein said C-terminal thioester or selenoester polypeptide is attached to a solid support.

18. The method of claim 3, wherein said C-terminal thioester or selenoester polypeptide comprises a polypeptide moiety selected from the group consisting of pramlintide moiety, exendin-4 moiety, davalintide moiety, glucagon-like peptide-1(7-37) [GLP-1(7-37)] moiety, meterleptin moiety, peptide-YY(3-36) [PYY(3-36)] moiety, gastric inhibitory polypeptide (GIP) moiety, insulin moiety, human growth hormone (UGH) moiety, erythropoietin (EPO) moiety, cholecystokinin (CCK) moiety, glucagon-like peptide-1 (GLP-2) moiety, GLP-1/glucagon chimeric peptide moiety, GLP-1/GIP chimeric peptide moiety, neurotensin moiety, urocortin moiety, neuromedin moiety, and hybrid thereof.

19. The method of claim 18, wherein said polypeptide moiety is the exendin-4 moiety.

* * * * *

SEQUENCE LISTING

<160> NUMBER OF SEQ ID NOS: 28

<210> SEQ ID NO 1
<211> LENGTH: 37
<212> TYPE: PRT
<213> ORGANISM: Rattus sp.

<400> SEQUENCE: 1

Lys Cys Asn Thr Ala Thr Cys Ala Thr Gln Arg Leu Ala Asn Phe Leu
1               5                   10                  15

Val Arg Ser Ser Asn Asn Leu Gly Pro Val Leu Pro Pro Thr Asn Val
            20                  25                  30

Gly Ser Asn Thr Tyr
        35

<210> SEQ ID NO 2
<211> LENGTH: 37
<212> TYPE: PRT
<213> ORGANISM: Homo sapiens

<400> SEQUENCE: 2

Lys Cys Asn Thr Ala Thr Cys Ala Thr Gln Arg Leu Ala Asn Phe Leu
1               5                   10                  15

Val His Ser Ser Asn Asn Phe Gly Ala Ile Leu Ser Ser Thr Asn Val
            20                  25                  30

Gly Ser Asn Thr Tyr
        35

<210> SEQ ID NO 3
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Lys Cys Asn Thr Ala Thr Cys Ala Thr Gln Arg Leu Ala Asn Phe Leu
1               5                   10                  15

Val His Ser Ser Asn Asn Phe Gly Pro Ile Leu Pro Pro Thr Asn Val
            20                  25                  30

-continued

Gly Ser Asn Thr Tyr
        35

<210> SEQ ID NO 4
<211> LENGTH: 32
<212> TYPE: PRT
<213> ORGANISM: Homo sapiens

<400> SEQUENCE: 4

Cys Gly Asn Leu Ser Thr Cys Met Leu Gly Thr Tyr Thr Gln Asp Phe
1               5                   10                  15

Asn Lys Phe His Thr Phe Pro Gln Thr Ala Ile Gly Val Gly Ala Pro
            20                  25                  30

<210> SEQ ID NO 5
<211> LENGTH: 32
<212> TYPE: PRT
<213> ORGANISM: Unknown
<220> FEATURE:
<223> OTHER INFORMATION: Description of Unknown: Salmon
      calcitonin peptide

<400> SEQUENCE: 5

Cys Ser Asn Leu Ser Thr Cys Val Leu Gly Lys Leu Ser Gln Glu Leu
1               5                   10                  15

His Lys Leu Gln Thr Tyr Pro Arg Thr Asn Thr Gly Ser Gly Thr Pro
            20                  25                  30

<210> SEQ ID NO 6
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Lys Cys Asn Thr Ala Thr Cys Val Leu Gly Arg Leu Ser Gln Glu Leu
1               5                   10                  15

His Arg Leu Gln Thr Tyr Pro Arg Thr Asn Thr Gly Ser Asn Thr Tyr
            20                  25                  30

<210> SEQ ID NO 7
<211> LENGTH: 39
<212> TYPE: PRT
<213> ORGANISM: Heloderma horridum
<220> FEATURE:
<223> OTHER INFORMATION: C-term NH2

<400> SEQUENCE: 7

His Ser Asp Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 8
<211> LENGTH: 39
<212> TYPE: PRT
<213> ORGANISM: Heloderma suspectum
<220> FEATURE:
<223> OTHER INFORMATION: C-term NH2

<400> SEQUENCE: 8

```
His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Ser
        35
```

<210> SEQ ID NO 9
<211> LENGTH: 31
<212> TYPE: PRT
<213> ORGANISM: Unknown
<220> FEATURE:
<223> OTHER INFORMATION: Description of Unknown: Glucagon-like peptide 1

<400> SEQUENCE: 9

```
His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly
            20                  25                  30
```

<210> SEQ ID NO 10
<211> LENGTH: 147
<212> TYPE: PRT
<213> ORGANISM: Unknown
<220> FEATURE:
<223> OTHER INFORMATION: Description of Unknown: Metreleptin peptide

<400> SEQUENCE: 10

```
Met Val Pro Ile Gln Lys Val Gln Asp Asp Thr Lys Thr Leu Ile Lys
1               5                   10                  15

Thr Ile Val Thr Arg Ile Asn Asp Ile Ser His Thr Gln Ser Val Ser
            20                  25                  30

Ser Lys Gln Lys Val Thr Gly Leu Asp Phe Ile Pro Gly Leu His Pro
        35                  40                  45

Ile Leu Thr Leu Ser Lys Met Asp Gln Thr Leu Ala Val Tyr Gln Gln
    50                  55                  60

Ile Leu Thr Ser Met Pro Ser Arg Asn Val Ile Gln Ile Ser Asn Asp
65                  70                  75                  80

Leu Glu Asn Leu Arg Asp Leu Leu His Val Leu Ala Phe Ser Lys Ser
                85                  90                  95

Cys His Leu Pro Trp Ala Ser Gly Leu Glu Thr Leu Asp Ser Leu Gly
            100                 105                 110

Gly Val Leu Glu Ala Ser Gly Tyr Ser Thr Glu Val Val Ala Leu Ser
        115                 120                 125

Arg Leu Gln Gly Ser Leu Gln Asp Met Leu Trp Gln Leu Asp Leu Ser
    130                 135                 140

Pro Gly Cys
145
```

<210> SEQ ID NO 11
<211> LENGTH: 36
<212> TYPE: PRT
<213> ORGANISM: Homo sapiens
<220> FEATURE:
<223> OTHER INFORMATION: C-term NH2

<400> SEQUENCE: 11

Ala Pro Leu Glu Pro Val Tyr Pro Gly Asp Asn Ala Thr Pro Glu Gln

-continued

```
                1               5                  10                  15
Met Ala Gln Tyr Ala Ala Asp Leu Arg Arg Tyr Ile Asn Met Leu Thr
            20                  25                  30
Arg Pro Arg Tyr
            35

<210> SEQ ID NO 12
<211> LENGTH: 36
<212> TYPE: PRT
<213> ORGANISM: Homo sapiens
<220> FEATURE:
<223> OTHER INFORMATION: C-term NH2

<400> SEQUENCE: 12

Tyr Pro Ile Lys Pro Glu Ala Pro Gly Glu Asp Ala Ser Pro Glu Glu
1               5                  10                  15
Leu Asn Arg Tyr Tyr Ala Ser Leu Arg His Tyr Leu Asn Leu Val Thr
            20                  25                  30
Arg Gln Arg Tyr
            35

<210> SEQ ID NO 13
<211> LENGTH: 36
<212> TYPE: PRT
<213> ORGANISM: Homo sapiens
<220> FEATURE:
<223> OTHER INFORMATION: C-term NH2

<400> SEQUENCE: 13

Tyr Pro Ser Lys Pro Asp Asn Pro Gly Glu Asp Ala Pro Ala Glu Asp
1               5                  10                  15
Met Ala Arg Tyr Tyr Ser Ala Leu Arg His Tyr Ile Asn Leu Ile Thr
            20                  25                  30
Arg Gln Arg Tyr
            35

<210> SEQ ID NO 14
<211> LENGTH: 42
<212> TYPE: PRT
<213> ORGANISM: Homo sapiens

<400> SEQUENCE: 14

Tyr Ala Glu Gly Thr Phe Ile Ser Asp Tyr Ser Ile Ala Met Asp Lys
1               5                  10                  15
Ile His Gln Gln Asp Phe Val Asn Trp Leu Leu Ala Gln Lys Gly Lys
            20                  25                  30
Lys Asn Asp Trp Lys His Asn Ile Thr Gln
            35                  40

<210> SEQ ID NO 15
<211> LENGTH: 110
<212> TYPE: PRT
<213> ORGANISM: Homo sapiens

<400> SEQUENCE: 15

Met Ala Leu Trp Met Arg Leu Leu Pro Leu Leu Ala Leu Leu Ala Leu
1               5                  10                  15
Trp Gly Pro Asp Pro Ala Ala Ala Phe Val Asn Gln His Leu Cys Gly
            20                  25                  30
Ser His Leu Val Glu Ala Leu Tyr Leu Val Cys Gly Glu Arg Gly Phe
            35                  40                  45
```

```
Phe Tyr Thr Pro Lys Thr Arg Arg Glu Ala Glu Asp Leu Gln Val Gly
    50                  55                  60

Gln Val Glu Leu Gly Gly Pro Gly Ala Gly Ser Leu Gln Pro Leu
65                  70                  75                  80

Ala Leu Glu Gly Ser Leu Gln Lys Arg Gly Ile Val Glu Gln Cys Cys
                85                  90                  95

Thr Ser Ile Cys Ser Leu Tyr Gln Leu Glu Asn Tyr Cys Asn
            100                 105                 110
```

<210> SEQ ID NO 16
<211> LENGTH: 217
<212> TYPE: PRT
<213> ORGANISM: Homo sapiens

<400> SEQUENCE: 16

```
Met Ala Thr Gly Ser Arg Thr Ser Leu Leu Leu Ala Phe Gly Leu Leu
1               5                   10                  15

Cys Leu Pro Trp Leu Gln Glu Gly Ser Ala Phe Pro Thr Ile Pro Leu
            20                  25                  30

Ser Arg Leu Phe Asp Asn Ala Met Leu Arg Ala His Arg Leu His Gln
        35                  40                  45

Leu Ala Phe Asp Thr Tyr Gln Glu Phe Glu Glu Ala Tyr Ile Pro Lys
    50                  55                  60

Glu Gln Lys Tyr Ser Phe Leu Gln Asn Pro Gln Thr Ser Leu Cys Phe
65                  70                  75                  80

Ser Glu Ser Ile Pro Thr Pro Ser Asn Arg Glu Glu Thr Gln Gln Lys
                85                  90                  95

Ser Asn Leu Glu Leu Leu Arg Ile Ser Leu Leu Leu Ile Gln Ser Trp
            100                 105                 110

Leu Glu Pro Val Gln Phe Leu Arg Ser Val Phe Ala Asn Ser Leu Val
        115                 120                 125

Tyr Gly Ala Ser Asp Ser Asn Val Tyr Asp Leu Leu Lys Asp Leu Glu
    130                 135                 140

Glu Gly Ile Gln Thr Leu Met Gly Arg Leu Glu Asp Gly Ser Pro Arg
145                 150                 155                 160

Thr Gly Gln Ile Phe Lys Gln Thr Tyr Ser Lys Phe Asp Thr Asn Ser
                165                 170                 175

His Asn Asp Asp Ala Leu Leu Lys Asn Tyr Gly Leu Leu Tyr Cys Phe
            180                 185                 190

Arg Lys Asp Met Asp Lys Val Glu Thr Phe Leu Arg Ile Val Gln Cys
        195                 200                 205

Arg Ser Val Glu Gly Ser Cys Gly Phe
    210                 215
```

<210> SEQ ID NO 17
<211> LENGTH: 217
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

```
Met Ala Thr Gly Ser Arg Thr Ser Leu Leu Leu Ala Phe Gly Leu Leu
1               5                   10                  15

Cys Leu Pro Trp Leu Gln Glu Gly Ser Ala Phe Pro Thr Ile Pro Leu
            20                  25                  30
```

Ser Arg Leu Phe Asp Asn Ala Met Leu Arg Ala His Arg Leu His Gln
        35                  40                  45

Leu Ala Phe Asp Thr Tyr Gln Glu Phe Glu Glu Ala Tyr Ile Pro Lys
    50                  55                  60

Glu Gln Lys Tyr Ser Phe Leu Gln Asn Pro Gln Thr Ser Leu Cys Phe
65                  70                  75                  80

Ser Glu Ser Ile Pro Thr Pro Ser Asn Arg Glu Glu Thr Gln Gln Lys
                85                  90                  95

Ser Asn Leu Glu Leu Leu Arg Ile Ser Leu Leu Leu Ile Gln Ser Trp
            100                 105                 110

Leu Glu Pro Val Gln Phe Leu Arg Ser Val Phe Ala Asn Ser Leu Val
        115                 120                 125

Tyr Gly Ala Ser Asp Ser Asn Val Tyr Asp Leu Leu Lys Asp Leu Glu
    130                 135                 140

Glu Gly Ile Gln Thr Leu Met Gly Arg Leu Glu Asp Gly Ser Pro Arg
145                 150                 155                 160

Thr Gly Gln Ile Phe Lys Gln Thr Tyr Ser Lys Phe Asp Thr Asn Ser
                165                 170                 175

His Asn Asp Asp Ala Leu Leu Lys Asn Tyr Gly Leu Leu Tyr Cys Phe
            180                 185                 190

Arg Lys Asp Met Asp Lys Val Glu Thr Phe Leu Arg Ile Val Gln Cys
        195                 200                 205

Arg Ser Val Glu Gly Ser Cys Gly Phe
    210                 215

<210> SEQ ID NO 18
<211> LENGTH: 115
<212> TYPE: PRT
<213> ORGANISM: Homo sapiens

<400> SEQUENCE: 18

Met Asn Ser Gly Val Cys Leu Cys Val Leu Met Ala Val Leu Ala Ala
1               5                   10                  15

Gly Ala Leu Thr Gln Pro Val Pro Pro Ala Asp Pro Ala Gly Ser Gly
            20                  25                  30

Leu Gln Arg Ala Glu Glu Ala Pro Arg Arg Gln Leu Arg Val Ser Gln
        35                  40                  45

Arg Thr Asp Gly Glu Ser Arg Ala His Leu Gly Ala Leu Leu Ala Arg
    50                  55                  60

Tyr Ile Gln Gln Ala Arg Lys Ala Pro Ser Gly Arg Met Ser Ile Val
65                  70                  75                  80

Lys Asn Leu Gln Asn Leu Asp Pro Ser His Arg Ile Ser Asp Arg Asp
                85                  90                  95

Tyr Met Gly Trp Met Asp Phe Gly Arg Arg Ser Ala Glu Glu Tyr Glu
            100                 105                 110

Tyr Pro Ser
        115

<210> SEQ ID NO 19
<211> LENGTH: 34
<212> TYPE: PRT
<213> ORGANISM: Homo sapiens

<400> SEQUENCE: 19

His Ala Asp Gly Ser Phe Ser Asp Glu Met Asn Thr Ile Leu Asp Asn
1               5                   10                  15

```
Leu Ala Ala Arg Asp Phe Ile Asn Trp Leu Ile Gln Thr Lys Ile Thr
             20                  25                  30

Asp Arg

<210> SEQ ID NO 20
<211> LENGTH: 170
<212> TYPE: PRT
<213> ORGANISM: Homo sapiens

<400> SEQUENCE: 20

Met Met Ala Gly Met Lys Ile Gln Leu Val Cys Met Leu Leu Leu Ala
1               5                   10                  15

Phe Ser Ser Trp Ser Leu Cys Ser Asp Ser Glu Glu Met Lys Ala
             20                  25                  30

Leu Glu Ala Asp Phe Leu Thr Asn Met His Thr Ser Lys Ile Ser Lys
             35                  40                  45

Ala His Val Pro Ser Trp Lys Met Thr Leu Leu Asn Val Cys Ser Leu
        50                  55                  60

Val Asn Asn Leu Asn Ser Pro Ala Glu Glu Thr Gly Glu Val His Glu
65                  70                  75                  80

Glu Glu Leu Val Ala Arg Arg Lys Leu Pro Thr Ala Leu Asp Gly Phe
                85                  90                  95

Ser Leu Glu Ala Met Leu Thr Ile Tyr Gln Leu His Lys Ile Cys His
            100                 105                 110

Ser Arg Ala Phe Gln His Trp Glu Leu Ile Gln Glu Asp Ile Leu Asp
        115                 120                 125

Thr Gly Asn Asp Lys Asn Gly Lys Glu Glu Val Ile Lys Arg Lys Ile
130                 135                 140

Pro Tyr Ile Leu Lys Arg Gln Leu Tyr Glu Asn Lys Pro Arg Arg Pro
145                 150                 155                 160

Tyr Ile Leu Lys Arg Asp Ser Tyr Tyr Tyr
                165                 170

<210> SEQ ID NO 21
<211> LENGTH: 124
<212> TYPE: PRT
<213> ORGANISM: Homo sapiens

<400> SEQUENCE: 21

Met Arg Gln Ala Gly Arg Ala Ala Leu Leu Ala Ala Leu Leu Leu Leu
1               5                   10                  15

Val Gln Leu Cys Pro Gly Ser Ser Gln Arg Ser Pro Glu Ala Ala Gly
             20                  25                  30

Val Gln Asp Pro Ser Leu Arg Trp Ser Pro Gly Ala Arg Asn Gln Gly
             35                  40                  45

Gly Gly Ala Arg Ala Leu Leu Leu Leu Ala Glu Arg Phe Pro Arg
        50                  55                  60

Arg Ala Gly Pro Gly Arg Leu Gly Leu Gly Thr Ala Gly Glu Arg Pro
65                  70                  75                  80

Arg Arg Asp Asn Pro Ser Leu Ser Ile Asp Leu Thr Phe His Leu Leu
                85                  90                  95

Arg Thr Leu Leu Glu Leu Ala Arg Thr Gln Ser Gln Arg Glu Arg Ala
            100                 105                 110

Glu Gln Asn Arg Ile Ile Phe Asp Ser Val Gly Lys
        115                 120
```

<210> SEQ ID NO 22
<211> LENGTH: 174
<212> TYPE: PRT
<213> ORGANISM: Homo sapiens

<400> SEQUENCE: 22

Met Leu Arg Thr Glu Ser Cys Arg Pro Arg Ser Pro Ala Gly Gln Val
1               5                   10                  15

Ala Ala Ala Ser Pro Leu Leu Leu Leu Leu Leu Leu Ala Trp Cys
            20                  25                  30

Ala Gly Ala Cys Arg Gly Ala Pro Ile Leu Pro Gln Gly Leu Gln Pro
        35                  40                  45

Glu Gln Gln Leu Gln Leu Trp Asn Glu Ile Asp Asp Thr Cys Ser Ser
    50                  55                  60

Phe Leu Ser Ile Asp Ser Gln Pro Gln Ala Ser Asn Ala Leu Glu Glu
65                  70                  75                  80

Leu Cys Phe Met Ile Met Gly Met Leu Pro Lys Pro Gln Glu Gln Asp
                85                  90                  95

Glu Lys Asp Asn Thr Lys Arg Phe Leu Phe His Tyr Ser Lys Thr Gln
            100                 105                 110

Lys Leu Gly Lys Ser Asn Val Val Ser Ser Val Val His Pro Leu Leu
        115                 120                 125

Gln Leu Val Pro His Leu His Glu Arg Arg Met Lys Arg Phe Arg Val
    130                 135                 140

Asp Glu Glu Phe Gln Ser Pro Phe Ala Ser Gln Ser Arg Gly Tyr Phe
145                 150                 155                 160

Leu Phe Arg Pro Arg Asn Gly Arg Arg Ser Ala Gly Phe Ile
                165                 170

<210> SEQ ID NO 23
<211> LENGTH: 153
<212> TYPE: PRT
<213> ORGANISM: Homo sapiens

<400> SEQUENCE: 23

Met Lys His Leu Arg Pro Gln Phe Pro Leu Ile Leu Ala Ile Tyr Cys
1               5                   10                  15

Phe Cys Met Leu Gln Ile Pro Ser Ser Gly Phe Pro Gln Pro Leu Ala
            20                  25                  30

Asp Pro Ser Asp Gly Leu Asp Ile Val Gln Leu Glu Gln Leu Ala Tyr
        35                  40                  45

Cys Leu Ser Gln Trp Ala Pro Leu Ser Arg Gln Pro Lys Asp Asn Gln
    50                  55                  60

Asp Ile Tyr Lys Arg Phe Leu Phe His Tyr Ser Arg Thr Gln Glu Ala
65                  70                  75                  80

Thr His Pro Val Lys Thr Gly Phe Pro Pro Val His Pro Leu Met His
                85                  90                  95

Leu Ala Ala Lys Leu Ala Asn Arg Arg Met Lys Arg Ile Leu Gln Arg
            100                 105                 110

Gly Ser Gly Thr Ala Ala Val Asp Phe Thr Lys Lys Asp His Thr Ala
        115                 120                 125

Thr Trp Gly Arg Pro Phe Phe Leu Phe Arg Pro Arg Asn Gly Arg Asn
    130                 135                 140

Ile Glu Asp Glu Ala Gln Ile Gln Trp
145                 150

<210> SEQ ID NO 24
<211> LENGTH: 121
<212> TYPE: PRT
<213> ORGANISM: Homo sapiens

<400> SEQUENCE: 24

```
Met Ala Arg Arg Ala Gly Gly Ala Arg Met Phe Gly Ser Leu Leu Leu
1               5                   10                  15

Phe Ala Leu Leu Ala Ala Gly Val Ala Pro Leu Ser Trp Asp Leu Pro
            20                  25                  30

Glu Pro Arg Ser Arg Ala Ser Lys Ile Arg Val His Ser Arg Gly Asn
        35                  40                  45

Leu Trp Ala Thr Gly His Phe Met Gly Lys Lys Ser Leu Glu Pro Ser
50                  55                  60

Ser Pro Ser His Trp Gly Gln Leu Pro Thr Pro Pro Leu Arg Asp Gln
65                  70                  75                  80

Arg Leu Gln Leu Ser His Asp Leu Leu Gly Ile Leu Leu Leu Lys Lys
                85                  90                  95

Ala Leu Gly Val Ser Leu Ser Arg Pro Ala Pro Gln Ile Gln Tyr Arg
            100                 105                 110

Arg Leu Leu Val Gln Ile Leu Gln Lys
        115                 120
```

<210> SEQ ID NO 25
<211> LENGTH: 32
<212> TYPE: PRT
<213> ORGANISM: Unknown
<220> FEATURE:
<223> OTHER INFORMATION: Description of Unknown: Gastric
      inhibitory polypeptide

<400> SEQUENCE: 25

```
Tyr Ala Glu Gly Thr Phe Ile Ser Asp Tyr Ser Ile Ala Met Asp Lys
1               5                   10                  15

Ile His Gln Gln Asp Phe Val Asn Trp Leu Leu Ala Gln Lys Gly Gly
            20                  25                  30
```

<210> SEQ ID NO 26
<211> LENGTH: 28
<212> TYPE: PRT
<213> ORGANISM: Heloderma suspectum

<400> SEQUENCE: 26

```
His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn
            20                  25
```

<210> SEQ ID NO 27
<211> LENGTH: 72
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

```
His Gly Glu Gly Thr Phe Thr Ser Asp Leu Ser Lys Gln Leu Glu Glu
1               5                   10                  15

Glu Ala Val Arg Leu Phe Ile Glu Trp Leu Lys Gln Gly Gly Pro Ser
            20                  25                  30
```

```
Lys Glu Ile Ile Ser Gly Gly Gly Lys Cys Asn Thr Ala Thr Cys Val
        35                  40                  45

Leu Gly Arg Leu Ser Gln Glu Leu His Arg Leu Gln Thr Tyr Pro Arg
    50                  55                  60

Thr Asn Thr Gly Ser Asn Thr Tyr
65                  70

<210> SEQ ID NO 28
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 28

His His His His His His
1               5
```